United States Patent
Xu et al.

(10) Patent No.: US 9,533,990 B2
(45) Date of Patent: *Jan. 3, 2017

(54) INHIBITORS OF SECRETION OF HEPATITIS B VIRUS ANTIGENS

(71) Applicants: DREXEL UNIVERSITY, Philadelphia, PA (US); BARUCH S. BLUMBERG INSTITUTE, Doylestown, PA (US); ENANTIGEN THERAPEUTICS, INC., Doylestown, PA (US)

(72) Inventors: Xiaodong Xu, Doylestown, PA (US); Andrea Cuconati, Oreland, PA (US); Timothy M. Block, Doylestown, PA (US); Tong Xiao, Edison, NJ (US)

(73) Assignees: Drexel University, Philadelphia, PA (US); Baruch S. Blumberg Institute, Doylestown, PA (US); Arbutus Biopharma, Inc., Doylestown, PA (US)

( * ) Notice: Subject to any disclaimer, the term of this patent is extended or adjusted under 35 U.S.C. 154(b) by 47 days.

This patent is subject to a terminal disclaimer.

(21) Appl. No.: 14/549,777

(22) Filed: Nov. 21, 2014

(65) Prior Publication Data
US 2015/0087659 A1  Mar. 26, 2015

Related U.S. Application Data

(63) Continuation of application No. 13/877,870, filed as application No. PCT/US2011/054726 on Oct. 4, 2011, now Pat. No. 8,921,381.

(60) Provisional application No. 61/389,321, filed on Oct. 4, 2010.

(51) Int. Cl.
*A61K 31/519* (2006.01)
*C07D 487/04* (2006.01)
*A61K 45/06* (2006.01)

(52) U.S. Cl.
CPC ........... *C07D 487/04* (2013.01); *A61K 31/519* (2013.01); *A61K 45/06* (2013.01)

(58) Field of Classification Search
CPC .......................... A61K 31/519; A61K 2300/00
USPC .................................................... 514/259.31
See application file for complete search history.

(56) References Cited

U.S. PATENT DOCUMENTS

| 5,484,760 A | 1/1996 | Bussler et al. |
| 6,020,338 A | 2/2000 | Pfrengle et al. |
| 8,921,381 B2 * | 12/2014 | Xu ............... A61K 45/06 514/259.31 |
| 2002/0068744 A1 | 6/2002 | Schmitt et al. |
| 2004/0219214 A1 | 11/2004 | Gravett et al. |
| 2009/0163545 A1 | 6/2009 | Goldfarb |

FOREIGN PATENT DOCUMENTS

| WO | WO2007044565 A2 | 4/2007 |
| WO | WO2007131168 A2 | 11/2007 |
| WO | WO2009060114 A1 | 5/2009 |
| WO | WO2010151799 A2 | 12/2010 |
| WO | WO2012047856 A3 | 4/2012 |

OTHER PUBLICATIONS

De Clercq, E. et al., "Antiviral Treatment of Chronic Hepatitis B Virus (HBV) Infections," Viruses, 2010, vol. 2(6), pp. 1279-1305.
Desenko, S.M. et al., "Partially Hydrogenated Aromatic Substituted Tetrazolo-[1,5-a]Pyrimidines," Chem. Heterocycl. Comp., 2001, vol. 37(6), pp. 747-754.
Dougherty, A.M. et al., "A Substituted Tetrahydro-Tetrazolo-Pyrimidine is a Specific and Novel Inhibitor of Hepatitis B Virus Surface Antigen Secretion," Antimicrobial Agents and Chemotherapy, 2007, vol. 51(12), pp. 4427-4437.
El-Koussi, N.A. et al., "Synthesis and Antibacterial Screening of Some 2,5,7-Triaryl-1,2,4-Triazolo[1,5-a] Pyrimidines," Bulletin of Pharmaceutical Sciences, Assiut University, 2004, vol. 27, pp. 141-154.
Orlov, V.D. et al., "Synthesis and Tautomerism of 5,7-Diaryl-4,7(6,7)-Dihydrotetrazolo[1,5a]Pyrimidines," Chemistry of Heterocyclic Compounds, 1988, vol. 11(24), pp. 1233-1237, p. 1234.
Shen, S-D. et al., "Ethyl 7-(4-bromo-phenyl)-5-trifluoro-methyl-4,7-Dihydro-tetrazolo[1,5-a]Pyrimidine-6-carboxylate," Acta Crystallogr. Sect. E., Struct. Reports Online, 2010, vol. E66, p. 02421.
Yu, W. et al., "Design, Synthesis and Biological Evaluation of Triazolo-pyrimidine Derivatives as Novel Inhibitors of Hepatitis B Virus Surface Antigen (HBsAg) Secretion," 2011, J. Med. Chem., vol. 54(16), pp. 5660-5670.
Supplementary European Search Report dated Feb. 25, 2014 for EP Application No. 11831427.7.
International Search Report dated Feb. 24, 2012 for International Application No. PCT/US2011/054726.

* cited by examiner

*Primary Examiner* — Raymond Henley, III

(74) *Attorney, Agent, or Firm* — Saul Ewing LLP; Kathryn Doyle; Domingos J. Silva

(57) ABSTRACT

Pharmaceutical compositions of the invention comprise triazolopyrimidines useful for the treatment of hepatitis virus in a patient.

13 Claims, No Drawings

SEQUENCE LISTING

<160> NUMBER OF SEQ ID NOS: 17

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gcctcagccc gtttctcctg gttcagttta ctag          34

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
caggagaaac gggctgaggc ccactcccat          30

<210> SEQ ID NO 3
<211> LENGTH: 46
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 3
ccaattttct tttgtctttg ggtgtacatt taacccctaa caaaac                     46

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acccaaagac aaagaaaat tggtaacagc ggt                                    33

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gttgctgtac caaaccttcg g                                                21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttcttgtgg caatgaccc                                                   19

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtctttgggt atacatttaa ccoctaacaa aac                                   33

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taaatgtata cccaaagaca aagaaaatt g                                      31

<210> SEQ ID NO 9
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
gggcctcagc ccgtttctca tggctcagtt tac                                    33

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagaaacggg ctgaggccca ctcccatagg                                        30

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cactgtttgg ctttcagtta tgtggatgat gtggt                                  35

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ataactgaaa gccaaacagt gggggaaagc c                                      31

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cactgtttgg ctttcagtta tatcgatgat gtggt                                  35

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtttctcat ggctcagttt ggtagtgcca tttc                                   34

<210> SEQ ID NO 15
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 15
aaactgagcc atgagaaacg ggctgaggcc                                          30

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cccccactgt ttggctttca tttatgtgga tg                                       32

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaaagccaaa cagtggggga aagccctacg                                          30
```

INHIBITORS OF SECRETION OF HEPATITIS B VIRUS ANTIGENS

CROSS-REFERENCE TO RELATED APPLICATIONS

This application is a continuation of, and claims priority to, U.S. patent application No. 13/877,870, filed Apr. 4, 2013, now issued as U.S. Pat. No. 8,921,381, which is the National Stage Entry of, and claims priority to, International Application No. PCT/US2011/054726, filed Oct. 4, 2011, which claims priority to U.S. Provisional Application No. 61/389,321, filed Oct. 4, 2010, wherein the contents of each of these applications are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Nov. 17, 2014, is named 101915.000575_SL.txt and is 4,237 bytes in size.

STATEMENT OF FEDERALLY FUNDED RESEARCH

The U.S. Government has a paid-up license in this invention and the right in limited circumstances to require the patent owner to license others on reasonable terms as provided for by the terms of grant number 1R43AI077123-01A1 awarded by the National Institute of Allergy and Infectious Diseases.

FIELD OF THE INVENTION

The present invention relates to compositions and methods for treating a hepatitis virus in a patient.

BACKGROUND OF THE INVENTION

Hepatitis B is one of the world's most prevalent diseases. Although most individuals seem to resolve the infection following acute symptoms, approximately 30% of cases become chronic. According to current estimates, 350-400 million people worldwide have chronic hepatitis B, leading to 500,000-1,000,000 deaths per year due largely to the development of hepatocellular carcinoma, cirrhosis, and other complications. Despite the availability of an effective vaccine, immunoglobulin therapy, interferon, and antiviral drugs, hepatitis B remains a major global health problem.

The causative agent is hepatitis B virus (HBV), a small DNA virus that is considered to be the prototypical member of the hepadnaviridae. HBV is an enveloped virus with an unusual mode of replication, centering on the establishment of a covalently closed circular DNA (cccDNA) copy of its genome in the host cell nucleus. This episomal form is established from conversion of the partially double stranded circular DNA (relaxed circular, or rcDNA) genome upon initial infection, and functions as the template for all HBV mRNAs. Unlike the mechanisms of most other DNA viruses, HBV cccDNA replicates through retrotranscription of a 1.1 genome unit-length RNA copy (pregenomic, or pgRNA) which is originally transcribed from the cccDNA template, and which is acted upon by a virus-encoded polymerase to yield progeny rcDNA. HBV DNA synthesis is coupled to assembly of its capsid, and most copies of the encapsidated genome then efficiently associate with the envelope proteins for virion assembly and secretion; a minority of these genomes are shunted to the nucleus where they are converted to cccDNA, thus amplifying levels of the episome.

As the only enzyme encoded by HBV, the polymerase has been well-exploited as a target for antiviral drug development, with four nucleoside-analogous polymerase inhibitors already FDA-approved, and others in development. Mutations in the primary sequence of the polymerase that confer resistance to lamivudine and adefovir have been identified clinically, and underlie a rebound of serum virus titers that 70% of treated patients experience within three years of starting lamivudine therapy. Although resistance to telbivudine, adefovir and entecavir occurs more rarely, it has been recorded. α-Interferon is the other major therapy available for hepatitis B, but is limited by poor long-term response and debilitating side effects. Hence, there is certainly a medical need for treatments with improved characteristics, and for a diversity of approaches in developing HBV therapies.

Aside from being a critical structural component of the virion, the HBV envelope is a major factor in the disease process. In chronically infected individuals, serum levels of HBV surface antigen (HBsAg) can be as high as 400 μg/ml, driven by the propensity for infected cells to secrete non-infectious subviral particles at levels far in excess of infectious (Dane) particles. HBsAg comprises the principal antigenic determinant in HBV infection and is composed of the small, middle and large surface antigens (S, M, and L, respectively). These proteins are produced from a single open reading frame as three separate N-glycosylated polypeptides through utilization of alternative transcriptional start sites (for L and M/S mRNAs) and initiation codons (for L, M and S).

Although the viral polymerase and HBsAg perform very different functions, both are essential proteins for the virus to complete its life cycle and be infectious. That is, HBV lacking HBsAg is completely defective and cannot infect or cause infection. HBsAg is needed to protect the virus nucleocapsid, to begin the infectious cycle, and to mediate morphogenesis and secretion of newly forming virus from the infected cell.

People who are chronically infected with HBV are usually characterized by readily detectable levels of circulating antibody specific to the viral capsid (HBc), with little, if any detectable levels of antibody to HBsAg. There is some evidence that chronic carriers do produce antibodies to HBsAg, but these antibodies are complexed with the circulating HBsAg, which can be present in milligram per milliliter amounts in a chronic carrier's circulation.

Reducing the amount of circulating levels of HBsAg might permit whatever anti-HBsA is present to gain a foothold and enable the antibody to manage the infection. Moreover, even if nucleocapsids, free of HBsAg, were to be expressed or secreted in to the circulation, perhaps as a result of cell death, the high levels of antiHBc would be expected to quickly complex with them and result in their clearance.

A study of duck hepatitis B virus (DHBV) has indicated that the presence of subviral particles in a culture of infected hepatocytes may have a transactivating function on viral genomic replication. In addition, a long-held tenet of HBV biology is that this circulating surface antigen functions to suppress virus-specific immune response. In chronic woodchuck hepatitis virus (WHY) infection, a reduction of antigenemia through clevudine treatment resulted in a positive response to vaccination indicating that circulating antigen may indeed suppress the immune response. Furthermore, the scarcity of virus-specific cytotoxic T lymphocytes (CTLs) that is a hallmark of chronic WHY and HBV infection may be due to repression of MHC I presentation by intracellular expression of L and M in infected hepatocytes. Existing FDA-approved therapies do not significantly affect HBsAg levels in the serum.

SUMMARY OF THE INVENTION

The present invention relates to pharmaceutical compositions of an effective amount of a compound selected from Formulas I, II, III, IV, V and VI and mixtures thereof:

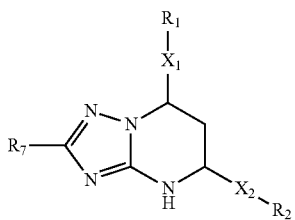

I

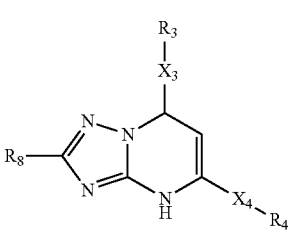

II

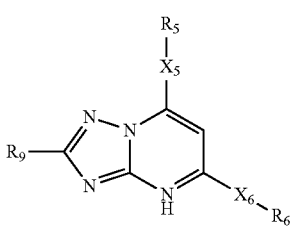

III

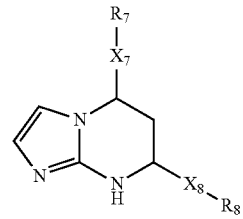

IV

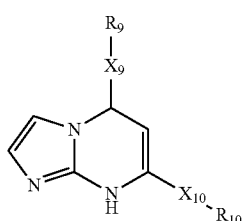

V

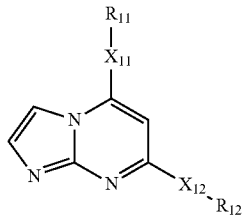

VI wherein $R_1$-$R_{12}$ are independently phenyl or Het, wherein each phenyl or Het is optionally substituted with at least one substituent independently selected from the group consisting of $(C_{1-7})$ alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, aryl, halo, $OR_a$, trifluoromethoxy, trifluoromethyl, $NO_2$, $NR_aR_b$, cyano, $CONR_aR_b$, $SO_mR_a$, $S(O)_mNR_aR_b$, $P(=O)(OR_a)(R_a)$, and Het, wherein $(C_{1-7})$ alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R$, $SO_mR_a$, $S(O)_mNR_aR_b$, or $P(=O)(OR_a)(R_a)$;

$X_1$-$X_{12}$ are independently a bond or a saturated or unsaturated alkylene group;

$R_a$ and $R_b$ are each independently H, $(C_{1-7})$alkyl, $(C_{3-12})$ cycloalkyl, $(C_{2-7})$alkanoyl, $(C_{2-7})$alkanoyloxy, or aryl, or $R_a$ and $R_b$ together with a nitrogen to which they are attached form a Het;

m is 0, 1, or 2;

n is 0, 1, 2, 3, or 4;

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative and (b) a pharmaceutically acceptable carrier.

Also provided are compounds of Formula VII

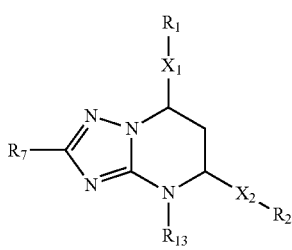

VII wherein $X_1$, $X_2$, $R_1$, $R_2$, $R_7$ are described as above;

$R_{13}$ is independently H, $(C_{1-7})$alkyl, $(C_{3-12})$cycloalkyl, $(C_{2-7})$alkanoyl, $(C_{2-7})$alkanoyloxy, or aryl;

Methods for treating a hepatitis virus in a patient by administering an effective amount of a compound of formulas I-VII to a patient in need thereof are also presented. In one embodiment, the method includes administering to the patient an effective amount of a compound of formulas I-VII that reduces the serum level of hepatitis B surface antigen (HBsAg) in the patient.

DETAILED DESCRIPTION OF THE INVENTION

The present invention relates to compositions and methods for treating a hepatitis virus in a patient.

As used above, and throughout the description of the invention, the following terms, unless otherwise indicated, shall be understood to have the following meanings:

"Patient" means a mammal including a human.

"Effective amount" means an amount of compound of the present invention effective for treating a hepatitis virus, and thus producing the desired therapeutic effect.

"Treat" or "treatment" or "treating" mean to lessen, eliminate, inhibit, improve, alter, or prevent a disease or condition, for example by administration of compound of the present invention.

"Alkyl" means aliphatic hydrocarbon group which may be branched or straight-chained having about 1 to about 10 carbon atoms. Preferred alkyl is "lower alkyl" having about 1 to about 3 carbon atoms; more preferred is methyl. Branched means that one or more lower alkyl groups such as methyl, ethyl, or propyl are attached to a linear alkyl chain. The alkyl group is also optionally substituted by alkoxy, halo, carboxy, hydroxy or $R_eR_fN$— (wherein $R_e$ and $R_f$ are independently hydrogen or alkyl, or $R_e$ and $R_f$ taken together with the nitrogen atom to which $R_e$ and $R_f$ are attached form azaheterocyclyl); and preferably optionally substituted by fluoro. Examples of alkyl include methyl, fluoromethyl, difluoromethyl, trifluoromethyl, ethyl, n-propyl, isopropyl, butyl, sec-butyl, t-butyl, amyl and hexyl.

"Cycloalkyl" means a non-aromatic monocyclic ring system of about 3 to about 7 carbon atoms. Preferred monocyclic cycloalkyl rings include cyclopentyl, cyclohexyl, and cycloheptyl; more preferred are cyclohexyl and cyclopentyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, hydroxy, halo, alkyl, alkoxy, carboxy, alkoxycarbonyl or $Y_1Y_2)NCO$—, wherein Y 1 and Y2 are independently hydrogen or alkyl.

"Het" is a four- (4), five- (5), six- (6), or seven- (7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring. Het includes "heteroaryl," which encompasses about a 5- to about a 10-membered aromatic monocyclic or bicyclic hydrocarbon ring system in which one to three of the atoms in a monocyclic ring system, and one to four of the atoms in a bicyclic ring system, is/are elements(s) other than carbon, for example nitrogen, oxygen or sulfur. The "heteroaryl" may also be substituted by one or more of the above-mentioned "aryl group substituents". Exemplary heteroaryl groups include substituted pyrazinyl, furanyl, thienyl, pyridyl, pyrimidinyl, isoxazolyl, isothiazolyl, oxazolyl, thiazoly, pyrazolyl, furazanyl, pyrrolyl, imidazo[2,1-b]thiazolyl, benzofurzanyl, indolyl, azaindolyl, benzimidazolyl, benzothienyl, quinolinyl, imidazolyl and isoquinolinyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and caproyl.

"Alkoxy" means an alkyl-O— group in which the alkyl group is as previously described. Preferred alkoxy is "lower alkoxy" having about 1 to about 3 carbon atoms; more preferred is methoxy. The alkoxy may be optionally substituted by one or more alkoxy, carboxy, alkoxycarbonyl, carboxyaryl or ReRfN— (wherein Re and Rf are as defined above). Exemplary alkoxy groups include methoxy, ethoxy, n-propoxy, i-propoxy, n-butoxy, heptoxy, 2-(morpholin-4-yl)ethoxy and 2-(ethoxy)ethoxy.

"Aryloxy" means aryl-O— group in which the aryl group is as previously described.

"Acyloxy" means and acyl-O— group in which the acyl group is as previously described.

"Carboxy" means a HO(O)C— (carboxylic acid) group.

"$R_eR_fN$—" means a substituted or unsubstituted amino group, wherein Re and Rf are as previously described. Exemplary groups include amino ($H_2N$—), methylamino, ethyl methylamino, dimethylamino and diethylamino.

"$R_eR_fNCO$—" means a substituted or unsubstituted carbamoyl group, wherein Re and Rf are as previously described. Exemplary groups are carbamoyl ($H_2NCO$—) are dimethylaminocarbamoyl ($Me_2NCO$—).

"AcylReN—" means an acylamino group wherein Re and acyl are as defined herein.

"Halo" means fluoro, chloro, bromo, or iodo. Preferred are fluoro, chloro or bromo, and more preferred are fluoro or chloro.

"Prodrug" means a form of the compound suitable for administration to a patient without undue toxicity, irritation, allergic response, and the like, and effective for their intended use. A prodrug is transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, et., Bioreversible Carriers in Drug Design, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

"Substituent of a ring structure" means any atom or group of atoms bonded to a ring in a molecule.

The present invention relates to pharmaceutical compositions of an effective amount of a compound selected from Formulas I, II, III, IV, V and VI and mixtures thereof:

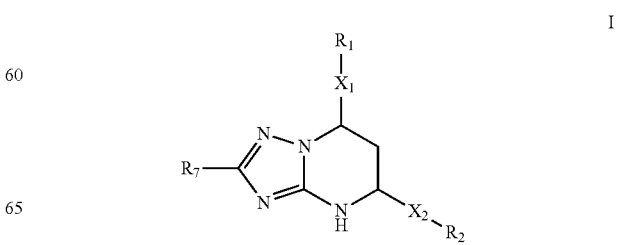

I

-continued

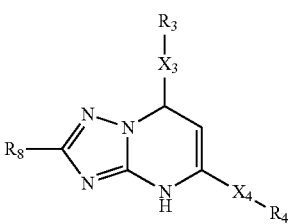
II

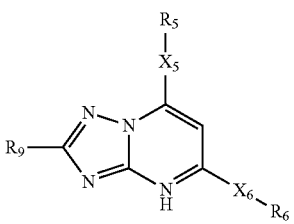
III

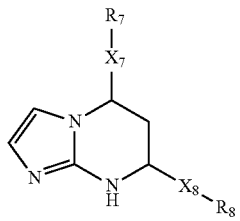
IV

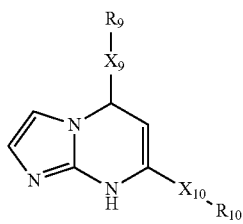
V

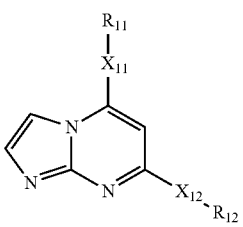
VI wherein
$R_1$-$R_{12}$ are independently phenyl or Het, wherein each phenyl or Het is optionally substituted with at least one substituent independently selected from the group consisting of ($C_{1-7}$)alkyl, ($C_{2-6}$)alkenyl, ($C_{2-6}$)alkynyl, ($C_{2-7}$) alkanoyl, ($C_{2-7}$)alkanoyloxy, ($C_{3-12}$)cycloalkyl, ($C_{1-7}$) acyl, aryl, halo, $OR_a$, trifluoromethoxy, trifluoromethyl, $NO_2$, $NR_aR_b$, cyano, $CONR_aR_b$, $SO_mR_a$, $S(O)mNR_aR_b$, $P(=O)(OR_a)(R_a)$, and Het, wherein ($C_{1-7}$)alkyl or ($C_{3-12}$)cycloalkyl are each independently optionally substituted with from 1 to 5 aryl, Het, $OR_a$, halo, $NO_2$, $NR_aR_b$, cyano, $CONR_aR_b$, $CO_2R$, $SO_mR_a$, $S(O)_mNR_aR_b$, or $P(=O)(OR_a)(R_a)$;
$X_1$-$X_{12}$ are independently a bond or a saturated or unsaturated alkylene group;
$R_a$ and $R_b$ are each independently H, ($C_{1-7}$)alkyl, ($C_{3-12}$) cycloalkyl, ($C_{2-7}$)alkanoyl, ($C_{2-7}$)alkanoyloxy, or aryl, or $R_a$ and $R_b$ together with a nitrogen to which they are attached form a Het;

m is 0, 1, or 2;
n is 0, 1, 2, 3, or 4;
or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative and
(b) a pharmaceutically acceptable carrier.
Also provided are compounds of Formula VII

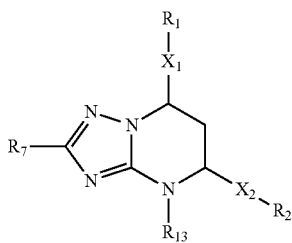
VII

Wherein
$X_1$, $X_2$, $R_1$, $R_2$, $R_7$ are described as above;
$R_{13}$ is independently H, ($C_{1-7}$)alkyl, ($C_{3-12}$)cycloalkyl, ($C_{2-7}$)alkanoyl, ($C_{2-7}$)alkanoyloxy, or aryl;
Exemplary embodiments include compounds or a pharmaceutically acceptable salt form thereof of the non-limiting examples defined herein below in Table 1.

TABLE 1

| Example number | Compound name |
|---|---|
| 1 | 7-(2-Chloro-6-fluorophenyl)-5-(4-chlorophenyl)-4,7-dihydro-[1,2,4]triazolo[1,5-a]pyrimidine |
| 2 | 5-(4-Chlorophenyl)-7-(2,6-dichlorophenyl)-4,7-dihydro-[1,2,4]triazolo[1,5-a]pyrimidine |
| 3 | 5-(4-Chlorophenyl)-7-(2,6-difluorophenyl)-4,7-dihydro-[1,2,4]triazolo[1,5-a]pyrimidine |
| 4 | 7-(2-Chloro-4-fluorophenyl)-5-(4-chlorophenyl)-4,7-dihydro-[1,2,4]triazolo[1,5-a]pyrimidine |
| 5 | 7-(2-Chloro-6-fluorophenyl)-5-(2-chlorophenyl)-4,7-dihydro-[1,2,4]triazolo[1,5-a]pyrimidine |
| 6 | 7-(2-Chloro-6-fluorophenyl)-5-(3-chlorophenyl)-4,7-dihydro-[1,2,4]triazolo[1,5-a]pyrimidine |
| 7 | 7-(2-Chloro-6-fluorophenyl)-5-(4-fluorophenyl)-4,7-dihydro-[1,2,4]triazolo[1,5-a]pyrimidine |
| 8 | 5-(4-Bromophenyl)-7-(2-chloro-6-fluorophenyl)-4,7-dihydro[1,2,4]triazolo[1,5-a]pyrimidine |
| 9 | 7-(2-Chloro-6-fluorophenyl)-5-(4-ethylphenyl)-4,7-dihydro-[1,2,4]triazolo[1,5-a]pyrimidine |
| 10 | 7-(2-Chloro-6-fluorophenyl)-5-(4-methoxyphenyl)-4,7-dihydro-[1,2,4]triazolo[1,5-a]pyrimidine |
| 11 | 5-([1,1'-Biphenyl]-4-yl)-7-(2-chloro-6-fluorophenyl)-4,7-dihydro-[1,2,4]triazolo[1,5-a]pyrimidine |
| 12 | 7-(2-Chloro-6-fluorophenyl)-5-(naphthalen-2-yl)-4,7-dihydro-[1,2,4]triazolo[1,5-a]pyrimidine |
| 13 | 7-(2-Chloro-6-fluorophenyl)-5-(3,4-dichlorophenyl)-4,7-dihydro-[1,2,4]triazolo[1,5-a]pyrimidine |
| 14 | 7-(2-Chloro-6-fluorophenyl)-5-(2,4-dichlorophenyl)-4,7-dihydro-[1,2,4]triazolo[1,5-a]pyrimidine |
| 15 | 7-(2-Chloro-6-fluorophenyl)-5-(2,4-difluorophenyl)-4,7-dihydro-[1,2,4]triazolo[1,5-a]pyrimidine |
| 16 | 7-(2-Chloro-6-fluorophenyl)-5-(3,4-dimethylphenyl)-4,7-dihydro-[1,2,4]triazolo[1,5-a]pyrimidine |
| 17 | 7-(2-Chloro-6-fluorophenyl)-5-(4-chlorophenyl)-[1,2,4]triazolo[1,5-a]pyrimidine |
| 18 | cis-7-(2-Chloro-6-fluorophenyl)-5-(4-chlorophenyl)-4,5,6,7-tetrahydro-[1,2,4]triazolo[1,5-a]pyrimidine |
| 19 | cis-5-(4-Chlorophenyl)-7-(2,6-dichlorophenyl)-4,5,6,7-tetrahydro-[1,2,4]triazolo[1,5-a]pyrimidine |

TABLE 1-continued

| Example number | Compound name |
|---|---|
| 20 | cis-5-(4-Chlorophenyl)-7-(2,6-difluorophenyl)-4,5,6,7-tetrahydro-[1,2,4]triazolo[1,5-a]pyrimidine |
| 21 | cis-7-(2-Chloro-4-fluorophenyl)-5-(4-chlorophenyl)-4,5,6,7-tetrahydro-[1,2,4]triazolo[1,5-a]pyrimidine |
| 22 | cis-7-(2-Chlorophenyl)-5-(4-chlorophenyl)-4,5,6,7-tetrahydro-[1,2,4]triazolo[1,5-a]pyrimidine |
| 23 | cis-5-(4-Chlorophenyl)-7-(4-isopropylphenyl)-4,5,6,7-tetrahydro-[1,2,4]triazolo[1,5-a]pyrimidine |
| 24 | cis-5-(4-Chlorophenyl)-7-phenyl-4,5,6,7-tetrahydro-[1,2,4]triazolo[1,5-a]pyrimidine |
| 25 | cis-7-(2-Chloro-6-fluorophenyl)-5-(2-chlorophenyl)-4,5,6,7-tetrahydro-[1,2,4]triazolo[1,5-a]pyrimidine |
| 26 | cis-7-(2-Chloro-6-fluorophenyl)-5-(3-chlorophenyl)-4,5,6,7-tetrahydro-[1,2,4]triazolo[1,5-a]pyrimidine |
| 27 | cis-7-(2-Chloro-6-fluorophenyl)-5-(4-fluorophenyl)-4,5,6,7-tetrahydro-[1,2,4]triazolo[1,5-a]pyrimidine |
| 28 | cis-5-(4-Bromophenyl)-7-(2-chloro-6-fluorophenyl)-4,5,6,7-tetrahydro-[1,2,4]triazolo[1,5-a]pyrimidine |
| 29 | cis-7-(2-Chloro-6-fluorophenyl)-5-(4-ethylphenyl)-4,5,6,7-tetrahydro-[1,2,4]triazolo[1,5-a]pyrimidine |
| 30 | cis-7-(2-Chloro-6-fluorophenyl)-5-(4-methoxyphenyl)-4,5,6,7-tetrahydro-[1,2,4]triazolo[1,5-a]pyrimidine |
| 31 | cis-5-([1,1-Biphenyl]-4-yl)-7-(2-chloro-6-fluorophenyl)-4,5,6,7-tetrahydro-[1,2,4]triazolo[1,5-a]pyrimidine |
| 32 | cis-7-(2-Chloro-6-fluorophenyl)-5-(naphthalen-2-yl)-4,5,6,7-tetrahydro-[1,2,4]triazolo[1,5-a]pyrimidine |
| 33 | cis-7-(2-Chloro-6-fluorophenyl)-5-(3,4-dichlorophenyl)-4,5,6,7-tetrahydro-[1,2,4]triazolo[1,5-a]pyrimidine |
| 34 | cis-7-(2-Chloro-6-fluorophenyl)-5-(2,4-dichlorophenyl)-4,5,6,7-tetrahydro-[1,2,4]triazolo[1,5-a]pyrimidine |
| 35 | cis-7-(2-Chloro-6-fluorophenyl)-5-(2,4-difluorophenyl)-4,5,6,7-tetrahydro-[1,2,4]triazolo[1,5-a]pyrimidine |
| 36 | cis-7-(2-Chloro-6-fluorophenyl)-5-(3,4-dimethylphenyl)-4,5,6,7-tetrahydro-[1,2,4]triazolo[1,5-a]pyrimidine |
| 37 | cis-7-(2-Chloro-6-fluorophenyl)-5-phenyl-4,5,6,7-tetrahydro-[1,2,4]triazolo[1,5-a]pyrimidine |
| 38 | cis-7-(2-Chloro-6-fluorophenyl)-5-(pyridin-2-yl)-4,5,6,7-tetrahydro-[1,2,4]triazolo[1,5-a]pyrimidine |
| 39 | cis-7-(2-Chloro-6-fluorophenyl)-5-(6-methoxypyridin-3-yl)-4,5,6,7-tetrahydro-[1,2,4]triazolo[1,5-a]pyrimidine |
| 40a | (R,S)-7-(2-Chloro-6-fluoro-phenyl)-5-(4-chloro-phenyl)-4,5,6,7-tetrahydro-[1,2,4]triazolo[1,5-a]pyrimidine |
| 40b | (S,R)-7-(2-Chloro-6-fluoro-phenyl)-5-(4-chloro-phenyl)-4,5,6,7-tetrahydro-[1,2,4]triazolo[1,5-a]pyrimidine |

For the purposes of demonstrating the manner in which the compounds of the present invention are named and referred to herein, the compound having the formula:

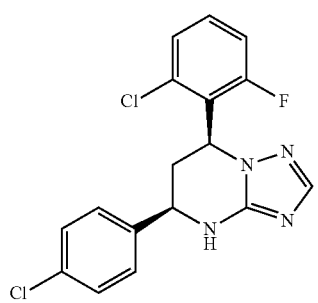 [SMILES: Fc1cccc(Cl)c1[C@@H]1C[C@H](c2ccc(Cl)cc2)Nc2ncnn21]

has the chemical name cis-7-(2-Chloro-6-fluorophenyl)-5-(4-chlorophenyl)-4,5,6,7-tetrahydro-[1,2,4]triazolo[1,5-a]pyrimidine.

For the purposes of the present invention, a compound depicted by the racemic formula, for example:

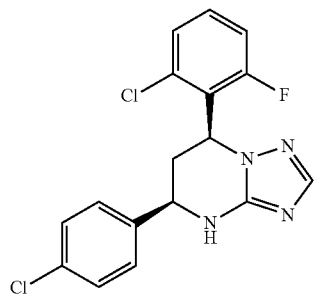

will stand equally well for either of the two enantiomers having the formula:

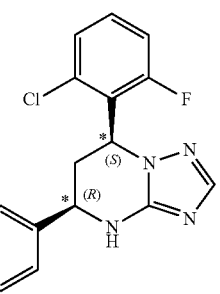

or the formula:

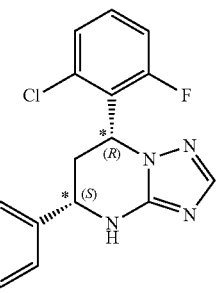

or mixtures thereof, or m the case where a third chiral center is present, all diastereomers.

For the purposes of demonstrating the manner in which the compounds of the present invention are named and referred to herein, the compound having the formula:

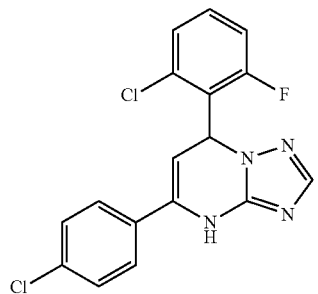

has the chemical name 7-(2-Chloro-6-fluorophenyl)-5-(4-chlorophenyl)-4,7-dihydro-[1,2,4]triazolo[1,5-a]pyrimidine.

For the purposes of the present invention, a compound depicted by the racemic formula, for example:

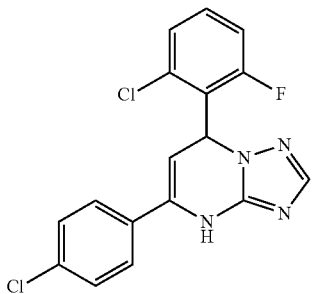

will stand equally well for either of the two enantiomers having the formula:

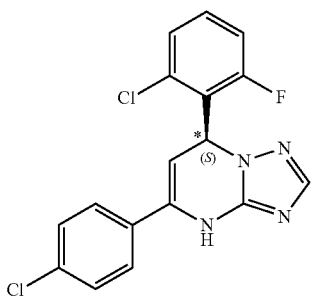

or the formula:

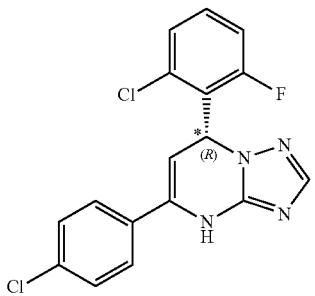

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The compounds of this invention may be prepared by employing procedures known in the literature starting from known compounds or readily prepared intermediates.

The compounds of formulas I-VII can be included in pharmaceutical compositions to treat, for example, a hepatitis virus in a patient. Examples of hepatitis viruses include viruses of the hepadnaviridae family, for example hepatitis B virus, and hepatitis delta virus.

In one embodiment, the pharmaceutical composition further includes an antiviral compound. In another embodiment, the antiviral compound is selected from nucleoside antiviral compounds, nucleotide antiviral compounds, and mixtures thereof.

Also provided is a method for treating a hepatitis virus in a patient by administering an effective amount of the compound of formulas I-VII to a patient in need thereof. An additional method for treating a hepatitis virus in a patient includes administering to the patient an effective amount of a compound of formula I that reduces the serum level of hepatitis B surface antigen (HBsAg) in the patient.

In practice, a composition containing a compound of formulas I-VII may be administered in any variety of suitable forms, for example, by inhalation, topically, parenterally, rectally, or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing a compound of formulas I-VII may be presented in forms permitting administration by the most suitable route. The invention also relates to administering compositions containing a compound of formulas I-VII which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of formulas I-VII in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of formulas I-VII may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound of formulas I-VII as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound of formulas I-vii in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the compound of formulas I-VII may be used. The compound of formulas I-VII may be also incorporated in a gel or matrix base for application in a patch, which would allow a controlled release of compound through transdermal barrier.

For administration by inhalation, the compound of formulas I-VII may be dissolved or suspended in a suitable carrier for use in a nebulizer or a suspension or solution aerosol, or may be absorbed or adsorbed onto a suitable solid carrier for use in a dry powder inhaler.

The percentage of compound of formulas I-VII in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound of formulas I-VII used in the invention may be administered as frequently as necessary in order to obtain the desired therapeutic effect. Some patients may respond rapidly to a higher or lower dose and may find much weaker maintenance doses adequate. For other patients, it may be necessary to have long term treatments at the rate of 1 to 4 doses per day, in accordance with the physiological requirements of each particular patient. Generally, the compound of formulas I-VII may be administered 1 to 4 times per day. Of course, for other patients, it will be necessary to prescribe not more than one or two doses per day.

Process

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H NMR spectra were recorded on 500 MHz or 300 MHz INOVA VARIAN (75 MHz for $^{13}$C NMR; 282 MHz for $^{19}$F NMR) spectrometer. Chemical shifts values are given in ppm and referred as the internal standard to TMS (tetramethylsilane). The peak patterns are indicated as follows: s, singlet; d, doublet; t, triplet; q, quadruplet; m, multiplet and dd, doublet of doublets. The coupling constants (1) are reported in Hertz (Hz). Melting points were determined with a national micromelting point apparatus without corrections. Mass Spectra were obtained on an Aligent LC-MS spectrometer (ES-API, Positive). Silica gel column chromatography was performed over silica gel 100-200 mesh, and the eluent was a mixture of ethyl acetate (EtOAc) and Hexanes. All the tested compounds possess a purity of at least 95% as determined by HPLC. Analytical HPLC was run on the Agilent 1100 HPLC instrument, equipped with Phenomenex® C12 column. Eluent system was: A (MeCN, 0.05% TFA) and C (H$_2$O, 0.05% TFA); flow rate=1 mL/min; Method A: 60% A, 40% C, A=219 nm; Method B: 70% A, 30% C, A=254 nm; Method C: 80% A, 20% C, A=254 nm. Retention times (tR) are given in minutes.

EXAMPLES

The examples below provide methods for preparing representative compounds of formula (I-VII). The skilled practitioner will know how to substitute the appropriate reagents, starting materials and purification methods known to those skilled in the art, in order to prepare additional compounds of the present invention.

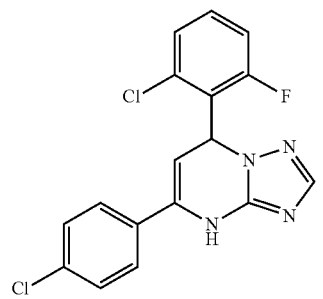 [SMILES: Fc1cccc(Cl)c1C1C=C(c2ccc(Cl)cc2)Nc2ncnn21]

Example 1

Synthesis of 7-(2-Chloro-6-fluorophenyl)-5-(4-chlorophenyl)-4,7-dihydro-[1,2,4]triazolo[1,5-a]pyrimidine. A solution of 1-(2-Chloro-6-fluoro-phenyl)-3-(4-chloro-phenyl)-propenone (5 mmol) and 3-amino-1,2,4-triazole (7.5 mmol) in DMF (5 mL) was refluxed for 2 h. The reaction mixture was cooled to room temperature, diluted with water (50 mL) and stirred sufficiently. The resulting mixture was filtered and washed with water to give the crude product, which was further purified either by recrystallization from EtOAc or through silica gel column chromatography (EtOAc/Hexanes 30:70) to afford the product as a white solid. Yield: 78%. m.p. 213-215° C. Rf=0.43 (EtOAc/Hexanes 50:50). MS: MH+=361. $^1$H NMR (300 MHz, DMSO-d$_6$): δ 10.16 (s, 1H, NH), 7.66-7.61 (m, 3H, CHar), 7.49-7.21 (m, 5H, CHar), 6.81-6.80 (m, 1H, CH=C), 5.19 (s, 1H, CH). HPLC: 99.5% (Method B, tR=5.75 min).

The non-limiting compounds examples 2-16 were prepared according to the procedures described in Examples 1 above using the corresponding reagents.

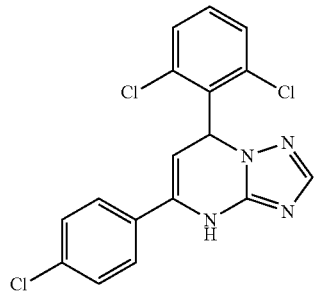

Example 2

5-(4-Chlorophenyl)-7-(2,6-dichlorophenyl)-4,7-dihydro-[1,2,4]triazolo[1,5-a]pyrimidine. Yield: 91%. m.p. 235° C. Rf=0.44 (EtOAc/Hexanes 50:50). MS: MH+=377. $^1$H NMR (300 MHz, DMSO-d$_6$): δ 10.20 (s, 1H, NH), 7.65-7.35 (m, 8H, CHar), 7.06 (d, J=3.6 Hz, 1H, CH=C), 5.10 (dd, J=3.3, 1.5 Hz, 1H, CH). HPLC: 99.9% (Method B, tR=6.64 min).

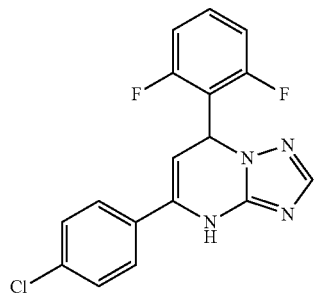 [SMILES: Fc1cccc(F)c1C1C=C(c2ccc(Cl)cc2)Nc2ncnn21]

Example 3

5-(4-Chlorophenyl)-7-(2,6-difluorophenyl)-4,7-dihydro-[1,2,4]triazolo[1,5-a]pyrimidine. Yield: 83%. m.p. 223-224° C. Rf=0.40 (EtOAc/Hexanes 50:50). MS: MH+=345. $^1$H NMR (300 MHz, DMSO-d$_6$): δ 10.13 (s, 1H, NH), 7.66-7.61 (m, 3H, CHar), 7.49-7.41 (m, 3H, CHar), 7.13-7.07 (m, 2H, CHar), 6.63 (d, J=3.6 Hz, 1H, CH=C), 5.26-5.25 (m, 1H, CH); $^{19}$F NMR (282 MHz, DMSO-d6): δ −118.26. $^{13}$C NMR (75 MHz, DMSO-d$_6$): δ 160.6 (dd, JC-F=247.9, 7.7 Hz, C), 150.5 (C), 150.4 (C), 135.9 (C), 134.3 (C), 133.5 (CH), 131.4 (t, JC-F=10.7 Hz, C), 129.2 (CH), 128.4 (CH), 117.2 (t, J C—F=15.2 Hz, C), 112.8 (d, J C—F=24.9 Hz, CH), 95.1 (CH), 50.8 (CH). HPLC: 98.8% (Method B, tR=4.96 min).

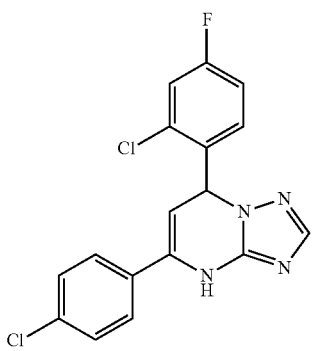 [SMILES: Fc1ccc(C2C=C(c3ccc(Cl)cc3)Nc3ncnn32)c(Cl)c1]

Example 4

7-(2-Chloro-4-fluorophenyl)-5-(4-chlorophenyl)-4,7-dihydro-[1,2,4]triazolo[1,5-a]pyrimidine. Yield: 83%. m.p. 250-251° C. Rf=0.17 (EtOAc/Hexanes 50:50). MS: MH+=361. 1H NMR (300 MHz, DMSO-$d_6$): δ 10.18 (d, J=1.5 Hz, 1H, NH), 7.69 (s, $^1$H, CHar), 7.64-7.61 (m, 2H, CHar), 7.49-7.46 (m, 3H, CHar), 7.25-7.22 (m, 2H, CHar), 6.57 (d, J=3.6 Hz, 1H, CH=C), 5.17 (dd, J=3.6, 1.5 Hz, 1H, CH). HPLC: 98.4% (Method B, tR=6.39 min).

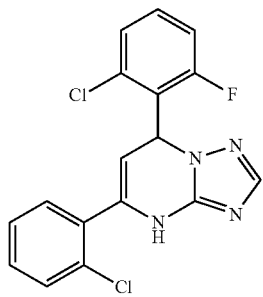 [SMILES: Fc1cccc(Cl)c1C1C=C(c2ccccc2Cl)Nc2ncnn21]

Example 5

7-(2-Chloro-6-fluorophenyl)-5-(2-chlorophenyl)-4,7-dihydro-[1,2,4]triazolo[1,5-a]pyrimidine. Yield: 77%. m.p. 192-193° C. Rf=0.40 (EtOAc/Hexanes 50:50). MS: MH+=361. $^1$H NMR (300 MHz, DMSO-$d_6$): δ 10.12 (s, 1H, NH), 7.63 (s, 1H, CHar), 7.54-7.25 (m, 7H, CHar), 6.57 (d, J=1.5 Hz, 1H, CH=C), 4.74 (s, 1H, CH). HPLC: 98.0% (Method B, tR=4.94 min).

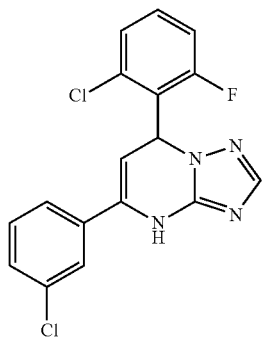 [SMILES: Fc1cccc(Cl)c1C1C=C(c2cccc(Cl)c2)Nc2ncnn21]

Example 6

7-(2-Chloro-6-fluorophenyl)-5-(3-chlorophenyl)-4,7-dihydro-[1,2,4]triazolo[1,5-a]pyrimidine. Yield: 88%. m.p. 246-248° C. Rf=0.36 (EtOAc/Hexanes 50:50). MS: MH+=361. $^1$H NMR (300 MHz, DMSO-$d_6$): δ 10.15 (s, 1H, NH), 7.66-7.17 (m, 8H, CHar), 6.78 (d, J=2.1 Hz, 1H, CH=C), 5.26 (s, 1H, CH). HPLC: 97.5% (Method B, tR=5.85 min)

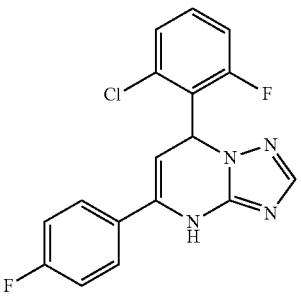 [SMILES: Fc1ccc(C2=CC(c3c(F)cccc3Cl)n3ncnc3N2)cc1]

Example 7

7-(2-Chloro-6-fluorophenyl)-5-(4-fluorophenyl)-4,7-dihydro-[1,2,4]triazolo[1,5-a]pyrimidine. Yield: 57%. m.p. 203-204° C. Rf=0.34 (EtOAc/Hexanes 50:50). MS: MH+=345. 1H NMR (300 MHz, DMSO-$d_6$): δ 10.13 (s, 1H, NH), 7.68-7.63 (m, 3H, CHar), 7.45-7.21 (m, 5H, CHar), 6.80-6.79 (m, 1H, CH=C), 5.12 (s, 1H, CH). HPLC: 96.4% (Method B, tR=4.62 min).

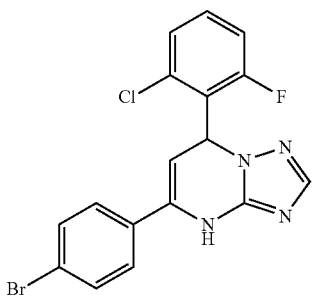

Example 8

5-(4-Bromophenyl)-7-(2-chloro-6-fluorophenyl)-4,7-dihydro-[1,2,4]triazolo[1,5-a]pyrimidine. Yield: 73%. m.p. 242-243° C. Rf=0.28 (EtOAc/Hexanes 50:50). MS: MH+=407. 1H NMR (300 MHz, DMSO-$d_6$): δ 10.16 (s, 1H, NH), 7.65-7.38 (m, 8H, CHar), 6.80 (d, J=1.8 Hz, 1H, CH=C), 5.19 (s, 1H, CH). HPLC: 99.6% (Method B, tR=6.57 min).

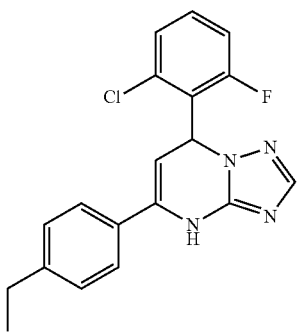 [SMILES: CCc1ccc(C2=CC(c3c(F)cccc3Cl)n3ncnc3N2)cc1]

Example 9

7-(2-Chloro-6-fluorophenyl)-5-(4-ethylphenyl)-4,7-dihydro-[1,2,4]triazolo[1,5-a]pyrimidine. Yield: 76%. m.p. 220-221° C. Rf=0.40 (EtOAc/Hexanes 50:50) MS: MH+=355. 1H NMR (300 MHz, DMSO-d$_6$): δ 10.15 (d, J=0.9 Hz, 1H, NH), 7.64 (s, $^1$H, CHar), 7.53-7.23 (m, 7H, CHar), 6.80-6.79 (m, 1H, CH=C), 5.81 (s, 1H, CH), 2.63 (q, J=1.8 Hz, 2H, CH2), 1.18 (t, J=7.5 Hz, 3H, CH3). HPLC: 99.1% (Method B, tR=6.15 mm).

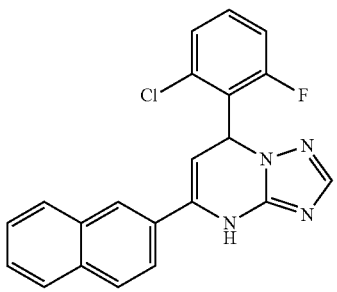

Example 10

7-(2-Chloro-6-fluorophenyl)-5-(4-methoxyphenyl)-4,7-dihydro-[1,2,4]triazolo[1,5-a]pyrimidine. Yield: 76%. m.p. 217-218° C. Rf=0.22 (EtOAc/Hexanes 50:50). MS: MH+=357. 1H NMR (300 MHz, DMSO-d$_6$): δ 10.02 (s, 1H, NH), 7.64-6.94 (m, 8H, CHar), 6.79-6.78 (m, 1H, CH=C), 5.03 (s, 1H, CH), 3.78 (s, 3H, OCH3). HPLC: 99.1% (Method B, tR=4.32 min).

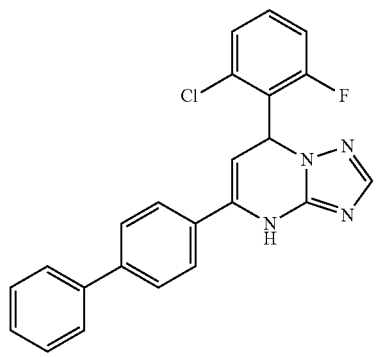 [SMILES: Fc1cccc(Cl)c1C1C=C(c2ccc(-c3ccccc3)cc2)Nc2ncnn21]

Example 11

5-([1,1'-Biphenyl]-4-yl)-7-(2-chloro-6-fluorophenyl)-4,7-dihydro-[1,2,4]triazolo[1,5-a]pyrimidine. Yield: 81%. m.p. 267° C. Rf=0.17 (EtOAc/Hexanes 50:50). MS: MH+=403. 1H NMR (300 MHz, DMSO-d$_6$): δ 10.17 (d, J=1.2 Hz, 1H, NH), 7.72-7.66 (m, 7H, CHar), 7.50-7.38 (m, 6H, CHar), 6.83 (m, 1H, CH=C), 5.22 (s, 1H, CH). HPLC: 99.1% (Method B, tR=7.85 min).

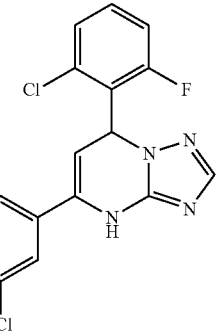

Example 12

7-(2-Chloro-6-fluorophenyl)-5-(naphthalen-2-yl)-4,7-dihydro-[1,2,4]triazolo[1,5-a]pyrimidine. Yield: 92%. m.p. 237° C. Rf=0.34 (EtOAc/Hexanes 50:50). MS: MH+=377. 1H NMR (300 MHz, DMSO-d$_6$): δ 10.25 (s, 1H, NH), 8.22 (s, 1H, CHar), 7.97-7.92 (m, 3H, CHar), 7.75-7.40 (m, 7H, CHar), 6.87 (d, J=1.8 Hz, 1H, CH=C), 5.33 (s, 1H, CH). HPLC: 98.9% (Method B, tR=6.45 min)

Example 13

7-(2-Chloro-6-fluorophenyl)-5-(3,4-dichlorophenyl)-4,7-dihydro-[1,2,4]triazolo[1,5-a]pyrimidine. Yield: 57%. m.p. 246-247° C. Rf=0.30 (EtOAc/Hexanes 50:50). MS: MH+=395. 1H NMR (300 MHz, DMSO-d$_6$): δ 10.20 (s, 1H, NH), 7.90 (d, 1=1.8 Hz, 1H, CHar), 7.69-7.19 (m, 6H, CHar), 6.82-6.80 (m, 1H, CH=C), 5.36 (s, 1H, CH). HPLC: 97.1% (Method B, tR=7.61 min)

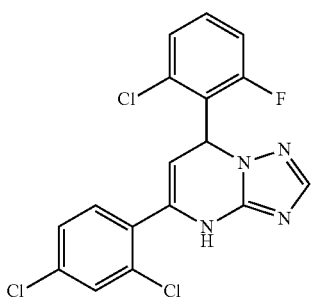 [SMILES: Fc1cccc(Cl)c1C1C=C(c2ccc(Cl)cc2Cl)Nc2ncnn21]

Example 14

7-(2-Chloro-6-fluorophenyl)-5-(2,4-dichlorophenyl)-4,7-dihydro-[1,2,4]triazolo[1,5-a]pyrimidine. Yield: 52%. m.p. 209-211° C. Rf=0.46 (EtOAc/Hexanes 50:50). MS: MH+=395. 1H NMR (300 MHz, DMSO-$d_6$): δ 10.14 (s, 1H, NH), 7.72-7.24 (m, 7H, CHar), 6.80 (d, J=1.8 Hz, 1H, CH=C), 4.79 (s, 1H, CH). HPLC: 95.0% (Method B, tR=6.80 min).

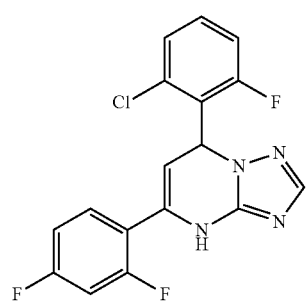 [SMILES: Fc1ccc(C2=CC(c3c(F)cccc3Cl)n3ncnc3N2)c(F)c1]

Example 15

7-(2-Chloro-6-fluorophenyl)-5-(2,4-difluorophenyl)-4,7-dihydro-[1,2,4]triazolo[1,5-a]pyrimidine. Yield: 66%. m.p. 186-188° C. Rf=0.46 (EtOAc/Hexanes 50:50). MS: MH+=363. 1H NMR (300 MHz, DMSO-$d_6$): δ 10.15 (s, 1H, NH), 7.64-7.11 (m, 7H, CHar), 6.81-6.80 (m, 1H, CH=C), 4.91 (s, 1H, CH). HPLC: 96.3% (Method B, tR=4.65 min).

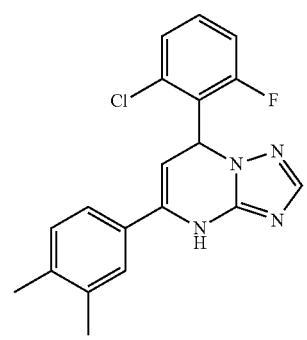 [SMILES: Cc1ccc(C2=CC(c3c(F)cccc3Cl)n3ncnc3N2)cc1C]

Example 16

7-(2-Chloro-6-fluorophenyl)-5-(3,4-dimethylphenyl)-4,7-dihydro-[1,2,4]triazolo[1,5-a]pyrimidine. Yield: 70%.

m.p. 217-218° C. Rf=0.40 (EtOAc/Hexanes 50:50). MS: MH+=355. 1H NMR (300 MHz, DMSO-$d_6$): δ 10.00 (s, 1H, NH), 7.64 (s, 1H, CHar), 7.42-7.14 (m, 6H, CHar), 6.79-6.78 (m, 1H, CH=C), 5.07 (s, 1H, CH). HPLC: 99.6% (Method B, tR=6.37 min).

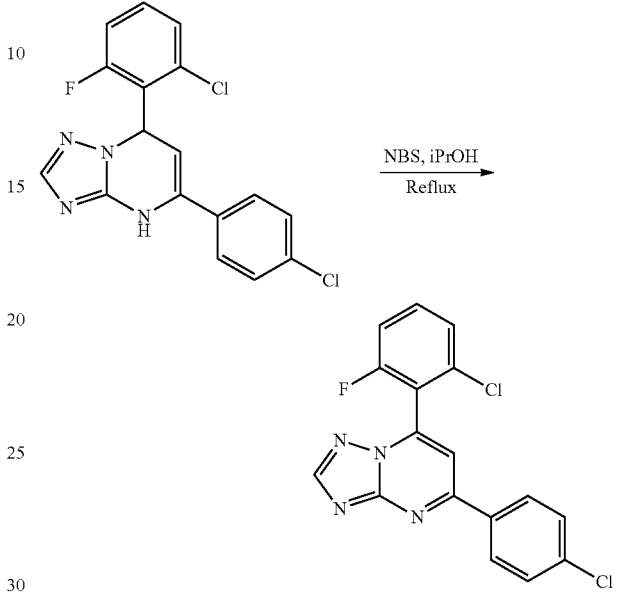

Example 17

Synthesis of 7-(2-Chloro-6-fluorophenyl)-5-(4-chlorophenyl)-[1,2,4]triazolo[1,5-a]pyrimidine. A sample of NBS (299 mg, 1.68 mmol) was added to a solution of 7-(2-Chloro-6-fluorophenyl)-5-(4-chlorophenyl)-4,7-dihydro-[1,2,4]triazolo[1,5-a]pyrimidine (3a) (101 mg, 0.28 mmol) in isopropanol (5 mL). The reaction mixture was refluxed for 36 h, then cooled to room temperature, treated with saturated NaHCO$_3$ solution 20 mL) and extracted with EtOAc (15 mL×3). The combined organic layer was dried OVER Na$_2$SO$_4$ and evaporated under reduced pressure. The given residue was purified through silica gel column chromatography (EtOAc/Hexanes 30:70) to afford a 42 mg white solid of 4a in 42% yield. m.p. 238-239° C. Rf=0.33 (EtOAc/Hexanes 30:70). MS: MH+=359. $^1$H NMR (500 MHz, CDCl$_3$): δ 8.48 (s, 1H, CHar), 8.15 (d, J=7.5 Hz, 2H, CHar), 7.57-7.39 (m, 5H, CHar), 7.20-7.19 (m, 1H, CHar). HPLC: 97.9% (Method C, tR=5.47 min).

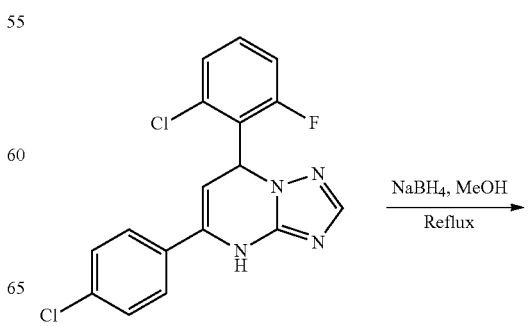

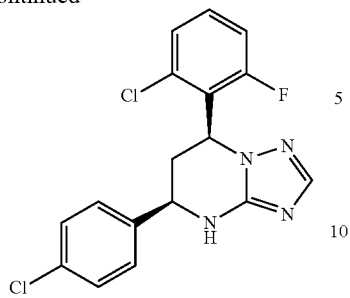

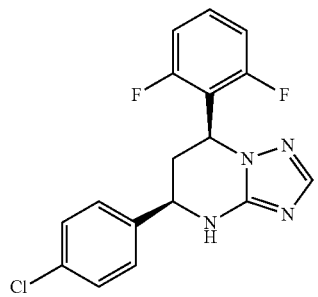

Example 20 cis-5-(4-Chlorophenyl)-7-(2,6-difluorophenyl)-4,5,6,7-tetrahydro[1,2,4]triazolo[1,5-a]pyrimidine. Yield: 84%. m.p. 245-246° C. Rf=0.19 (EtOAc/Hexanes 75:25). MS: MH+=347. $^1$H NMR (500 MHz, DMSO-$d_6$): δ 7.52-7.11 (m, 8H, CHar), 5.80 (dd, J=11.0, 4.5 Hz, 1H, CH), 4.79 (d, J=11.0 Hz, 1H, CH), 2.46-2.18 (m, 2H, CH$_2$). HPLC: 98.9% (Method A, tR=3.35 min).

Example 18

Synthesis of cis-7-(2-Chloro-6-fluorophenyl)-5-(4-chlorophenyl)-4,5,6,7-tetrahydro-[1,2,4]triazolo[1,5-a]pyrimidine. Sodium borohydride (10 mmol) was added to a suspension of 7-(2-Chloro-6-fluorophenyl)-5-(4-chlorophenyl)-4,7-dihydro-[1,2,4]triazolo[1,5-a]pyrimidine (1 mmol) in methanol (5 mL). The reaction mixture was refluxed for 30 min, then cooled to room temperature, diluted with water (50 mL) and stirred sufficiently. The resulting mixture was filtered and washed with water to give the crude product, which was further purified by recrystallization from a mixture of EtOAc and Hexanes to provide the product as a white solid. Yield: 89%. m.p. 227-228° C. Rf=0.16 (EtOAc/Hexanes 33.3:66.7). MS: MH+=363. $^1$H NMR (500 MHz, DMSO-$d_6$): δ 7.54-7.15 (m, 8H, CHar), 5.98-5.94 (m, 1H, CH), 4.82-4.78 (m, 1H, CH), 2.47-2.13 (m, 2H, CH2). HPLC: 99.8% (Method A, tR=3.67 min).

The non-limiting compounds examples 19-39 were prepared according to the procedures described in Examples 18 above using the corresponding reagents.

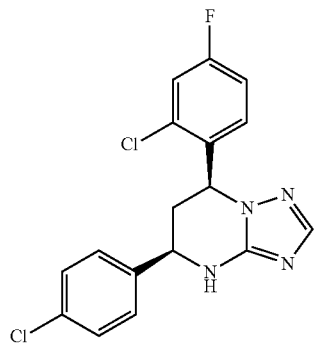 [SMILES: Fc1ccc([C@@H]2C[C@H](c3ccc(Cl)cc3)Nc3ncnn32)c(Cl)c1]

Example 21 cis-7-(2-Chloro-4-fluorophenyl)-5-(4-chlorophenyl)-4,5,6,7-tetrahydro-[1,2,4]triazolo[1,5-a]pyrimidine. Yield: 94%. m.p. 224-225° C. Rf=0.14 (EtOAc/Hexanes 75:25). MS: MH+=363. $^1$H NMR (500 MHz, DMSO-$d_6$): δ 7.58-7.17 (m, 8H, CHar), 5.73 (d, J=3.5 Hz, 1H, CH), 4.78 (d, J=10.5 Hz, 1H, CH), 2.44-2.18 (m, 2H, CH2). HPLC: 96.8% (Method A, tR=4.12 min).

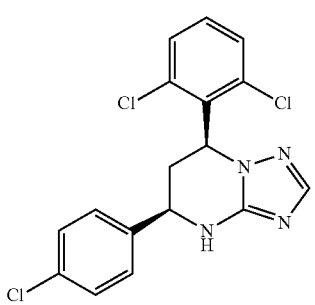

Example 19 cis-5-(4-Chlorophenyl)-7-(2,6-dichlorophenyl)-4,5,6,7-tetrahydro-[1,2,4]triazolo[1,5-a]pyrimidine. Yield: 88%. m.p. 246-247° C. Rf=0.19 (EtOAc/Hexanes 75:25). MS: MH+=379. $^1$H NMR (500 MHz, DMSO-$d_6$): δ 7.55-7.35 (m, 8H, CHar), 6.17 (dd, J=11.0, 6.5 Hz, 1H, CH), 4.81 (d, J=10.0 Hz, 1H, CH), 2.42-2.30 (m, 2H, CH$_2$). HPLC: 98.2% (Method A, tR=4.10 min).

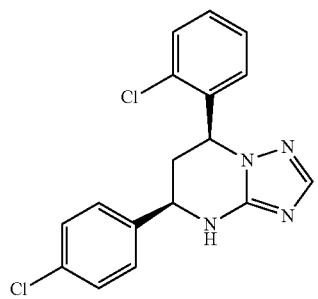 [SMILES: Clc1ccc([C@H]2C[C@@H](c3ccccc3Cl)n3ncnc3N2)cc1]

Example 22 cis-7-(2-Chlorophenyl)-5-(4-chlorophenyl)-4,5,6,7-tetrahydro[1,2,4]triazolo[1,5-a]pyrimidine. Yield: 68%. m.p. 202-204° C. Rf=0.14 (EtOAc/Hexanes 75:25). MS: MH+=345. ¹H NMR (500 MHz, DMSO-$d_6$): δ 7.56-7.27 (m, 9H, CHar), 7.08 (s, 1H, NH), 5.75 (s, 1H, CH), 4.78 (d, J=10.5 Hz, 1H, CH), 2.46-2.16 (m, 2H, CH2). HPLC: 98.8% (Method A, tR=3.63 min).

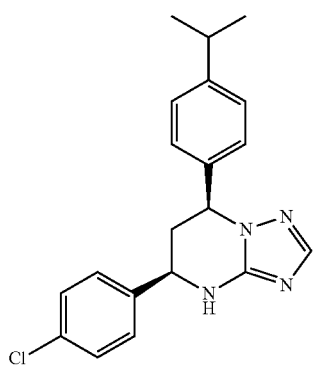 [SMILES: CC(C)c1ccc([C@@H]2C[C@H](c3ccc(Cl)cc3)Nc3ncnn32)cc1]

Example 23 cis-5-(4-Chlorophenyl)-7-(4-isopropylphenyl)-4,5,6,7-tetrahydro[1,2,4]triazolo[1,5-a]pyrimidine. Yield: 75%. m.p. 194-195° C. Rf=0.09 (EtOAc/Hexanes 75:25). MS: MH+=353. ¹H NMR (500 MHz, DMSO-d6): δ 7.47-7.44 (m, 3H, CHar), 7.41-7.38 (m, 2H, CHar), 7.18 (d, J=8.0 Hz, 2H, CHar), 7.11 (d, J=8.0 Hz, 2H, CHar), 5.34 (dd, J=10.5, 5.0 Hz, 1H, CH), 4.70 (dd, J=11.5, 2.5 Hz, 1H, CH), 2.90-2.82 (m, 1H, CH), 2.42-2.07 (m, 2H, CH2), 1.18 (d, J=7.0 Hz, 6H, CH3). HPLC: 99.8% (Method A, tR=4.99 min).

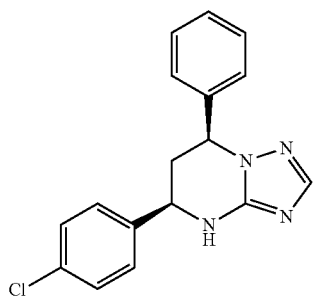 [SMILES: Clc1ccc([C@H]2C[C@@H](c3ccccc3)n3ncnc3N2)cc1]

Example 24 cis-5-(4-Chlorophenyl)-7-phenyl-4,5,6,7-tetrahydro-[1,2,4]triazolo[1,5-a]pyrimidine. Yield: 77%. m.p. 210-212° C. Rf=0.09 (EtOAc/Hexanes 75:25). MS: MH+=311. ¹H NMR (500 MHz, DMSO-$d_6$): δ 7.48-7.46 (m, 3H, CHar), 7.42-7.39 (m, 2H, CHar), 7.35-7.26 (m, 3H, CHar), 7.22-7.20 (m, 2H, CHar), 5.40-5.37 (m, 1H, CH), 4.71 (dd, J=11.0, 2.5 Hz, 1H, CH), 2.45-2.06 (m, 2H, CH2). HPLC: 99.8% (Method A, tR=3.11 min).

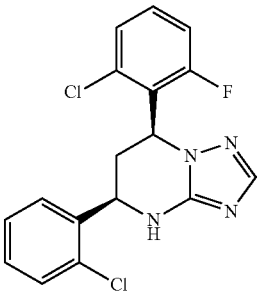 [SMILES: Fc1cccc(Cl)c1[C@@H]1C[C@H](c2ccccc2Cl)Nc2ncnn21]

Example 25 cis-7-(2-Chloro-6-fluorophenyl)-5-(2-chlorophenyl)-4,5,6,7-tetrahydro-[1,2,4]triazolo[1,5-a]pyrimidine. Yield: 90%. m.p. 271-272° C. Rf=0.17 (EtOAc/Hexanes 33.3:66.7). MS: MH+=363. ¹H NMR (500 MHz, DMSO-$d_6$): δ 7.70-7.15 (m, 8H, CHar), 6.05-6.00 (m, 1H, CH), 5.16-5.13 (m, 1H, CH), 2.47-2.08 (m, 2H, CH2). HPLC: 99.4% (Method A, tR=3.64 min).

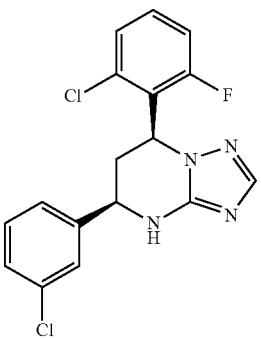 [SMILES: Fc1cccc(Cl)c1[C@@H]1C[C@H](c2cccc(Cl)c2)Nc2ncnn21]

Example 26 cis-7-(2-Chloro-6-fluorophenyl)-5-(3-chlorophenyl)-4,5,6,7-tetrahydro-[1,2,4]triazolo[1,5-a]pyrimidine. Yield: 80%. m.p. 262-263° C. Rf=0.13 (EtOAc/Hexanes 33.3:66.7). MS: MH+=363. ¹H NMR (500 MHz, DMSO-$d_6$): δ 7.56-7.17 (m, 8H, CHar), 5.94 (s, 1H, CH), 4.81 (s, 1H, CH), 2.48-2.15 (m, 2H, CH2). HPLC: 99.7% (Method A, tR=3.16 min).

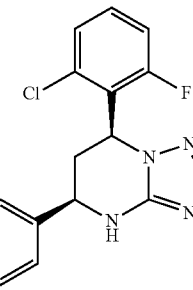

Example 27 cis-7-(2-Chloro-6-fluorophenyl)-5-(4-fluorophenyl)-4,5,6,7-tetrahydro-[1,2,4]triazolo[1,5-a]pyrimidine. Yield: 68%.

m.p. 240-241° C. Rf=0.22 (EtOAc/Hexanes 75:25). MS: MH+=347. ¹H NMR (500 MHz, DMSO-d6): δ 7.52-7.15 (m, 8H, CHar), 5.98-5.93 (m, 1H, CH), 4.82-4.78 (m, 1H, CH), 2.48-2.14 (m, 2H, CH₂). HPLC: 98.4% (Method A, tR=3.86 min).

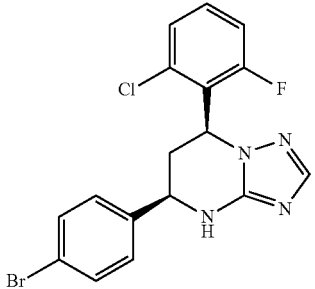

Example 28 cis-5-(4-Bromophenyl)-7-(2-chloro-6-fluorophenyl)-4,5,6,7-tetrahydro-[1,2,4]triazolo[1,5-a]pyrimidine. Yield: 64%. m.p. 246-247° C. Rf=0.22 (EtOAc/Hexanes 75:25). MS: MH+=409. ¹H NMR (500 MHz, DMSO-d₆): δ 7.58-7.15 (m, 8H, CHar), 5.97-5.95 (m, 1H, CH), 4.80-4.77 (m, 1H, CH), 2.43-2.15 (m, 2H, CH₂). HPLC: 99.5% (Method A, tR=4.09 min).

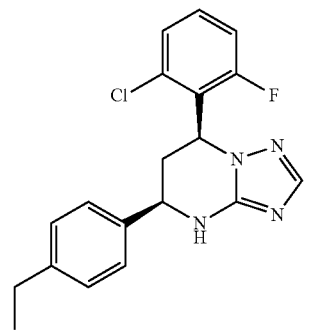 [SMILES: CCc1ccc([C@H]2C[C@@H](c3c(F)cccc3Cl)n3ncnc3N2)cc1]

Example 29 cis-7-(2-Chloro-6-fluorophenyl)-5-(4-ethylphenyl)-4,5,6,7-tetrahydro-[1,2,4]triazolo[1,5-a]pyrimidine. Yield: 90%. m.p. 230-231° C. Rf=0.28 (EtOAc/Hexanes 75:25). MS: MH+=357. ¹H NMR (500 MHz, DMSO-d₆): δ 7.44-7.15 (m, 8H, CHar), 5.97-5.93 (m, 1H, CH), 4.75-4.72 (m, 1H, CH), 2.60 (q, J=7.5 Hz, 2H, CH2), 2.47-2.15 (m, 2H, CH2), 1.17 (t, J=7.5 Hz, 3H, CH3). HPLC: 99.8% (Method A, tR=3.67 min).

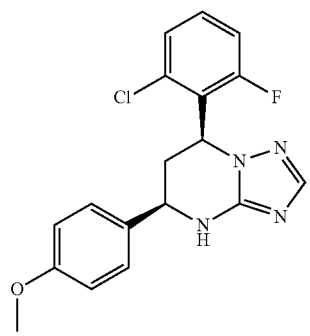 [SMILES: COc1ccc([C@H]2C[C@@H](c3c(F)cccc3Cl)n3ncnc3N2)cc1]

Example 30 cis-7-(2-Chloro-6-fluorophenyl)-5-(4-methoxyphenyl)-4,5,6,7-tetrahydro-[1,2,4]triazolo[1,5-a]pyrimidine. Yield: 86%. m.p. 221-222° C. Rf=0.20 (EtOAc/Hexanes 75:25). MS: MH+=359. ¹H NMR (500 MHz, DMSO-d₆): δ 7.41-6.93 (m, 8H, CHar), 5.96-5.92 (m, 1H, CH), 4.72 (d, J=10.5 Hz, 1H, CH), 3.75 (s, 3H, OCH3), 2.46-2.14 (m, 2H, CH2). HPLC: 99.4% (Method A, tR=3.03 min).

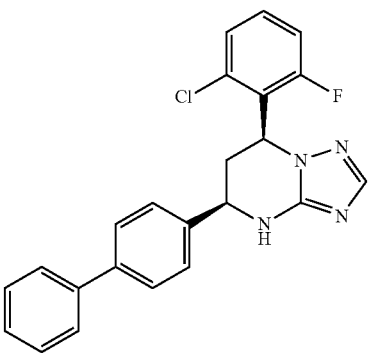 [SMILES: Fc1cccc(Cl)c1[C@@H]1C[C@H](c2ccc(-c3ccccc3)cc2)Nc2ncnn21]

Example 31 cis-5-([1,1'-Biphenyl]-4-yl)-7-(2-chloro-6-fluorophenyl)-4,5,6,7-tetrahydro-[1,2,4]triazolo[1,5-a]pyrimidine. Yield: 84%. m.p. 213-215° C. Rf=0.20 (EtOAc/Hexanes 75:25). MS: MH+=405. ¹H NMR (500 MHz, DMSO-d₆): δ 7.69-7.16 (m, ¹³H, CHar), 6.01-5.97 (m, 1H, CH), 4.85-4.82 (m, 1H, CH), 2.47-2.21 (m, 2H, CH2). HPLC: 99.0% (Method A, tR=4.92 min).

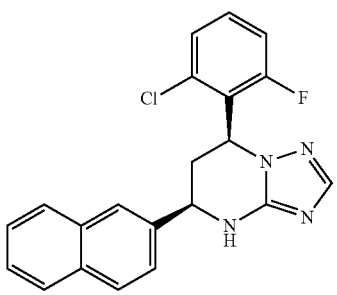 [SMILES: Fc1cccc(Cl)c1[C@@H]1C[C@H](c2ccc3ccccc3c2)Nc2ncnn21]

Example 32 cis-7-(2-Chloro-6-fluorophenyl)-5-(naphthalen-2-yl)-4,5,6,7-tetrahydro-[1,2,4]triazolo[1,5-a]pyrimidine. 72%. m.p. 224-225° C. Rf=0.31 (EtOAc/Hexanes 75:25). MS: MH+=379. ¹H NMR (500 MHz, DMSO-d₆): δ 8.01-7.16 (m, 11H, CHar), 6.05-6.00 (m, 1H, CH), 4.98-4.95 (m, 1H, CH), 2.61-2.27 (m, 2H, CH2, overlapped with the peaks of DMSO). HPLC: 99.6% (Method A, tR=4.02 min).

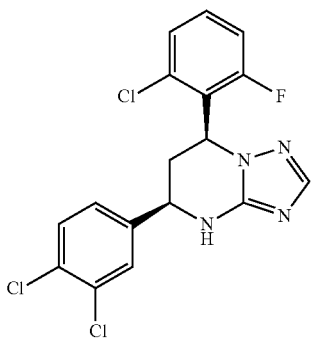 [SMILES: Fc1cccc(Cl)c1[C@@H]1C[C@H](c2ccc(Cl)c(Cl)c2)Nc2ncnn21]

Example 33 cis-7-(2-Chloro-6-fluorophenyl)-5-(3,4-dichlorophenyl)-4,5,6,7-tetrahydro-[1,2,4]triazolo[1,5-a]pyrimidine. Yield: 77%. m.p. 252-254° C. Rf=0.21 (EtOAc/Hexanes 75:25). MS: MH+=397. $^1$H NMR (500 MHz, DMSO-d$_6$): δ 7.72-7.15 (m, 7H, CHar), 5.97-5.92 (m, 1H, CH), 4.84-4.80 (m, 1H, CH), 2.47-2.14 (m, 2H, CH$_2$). HPLC: 99.7% (Method A, tR=4.56 min).

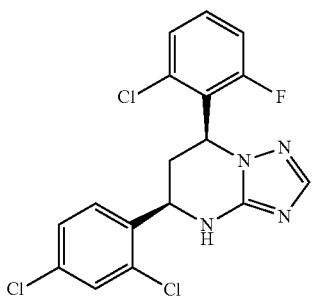 [SMILES: Fc1cccc(Cl)c1[C@@H]1C[C@H](c2ccc(Cl)cc2Cl)Nc2ncnn21]

Example 34 cis-7-(2-Chloro-6-fluorophenyl)-5-(2,4-dichlorophenyl)-4,5,6,7-tetrahydro-[1,2,4]triazolo[1,5-a]pyrimidine. Yield: 88%. m.p. 267-269° C. Rf=0.22 (EtOAc/Hexanes 33.3:66.7). MS: MH+=397. $^1$H NMR (500 MHz, DMSO-d$_6$): δ 7.70-7.15 (m, 7H, CHar), 6.05-6.00 (m, 1H, CH), 5.14-5.11 (m, 1H, CH), 2.49-2.09 (m, 2H, CH$_2$). HPLC: 98.7% (Method A, tR=4.96 min).

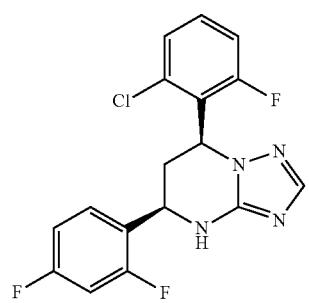 [SMILES: Fc1ccc([C@H]2C[C@@H](c3c(F)cccc3Cl)n3ncnc3N2)c(F)c1]

Example 35 cis-7-(2-Chloro-6-fluorophenyl)-5-(2,4-difluorophenyl)-4,5,6,7-tetrahydro-[1,2,4]triazolo[1,5-a]pyrimidine. Yield: 92%. m.p. 225° C. Rf=0.28 (EtOAc/Hexanes 75:25). MS: MH+=365. $^1$H NMR (500 MHz, DMSO-d$_6$): δ 7.65-7.12 (m, 7H, CHar), 6.04-5.99 (m, 1H, CH), 5.05 (d, J=10.5 Hz, 1H, CH), 2.43-2.23 (m, 2H, CH$_2$). HPLC: 99.1% (Method A, tR=3.37 min).

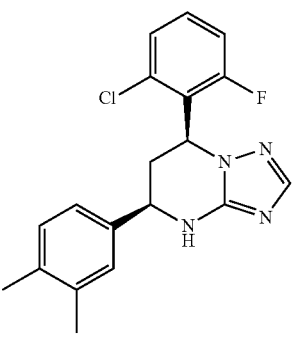 [SMILES: Cc1ccc([C@H]2C[C@@H](c3c(F)cccc3Cl)n3ncnc3N2)cc1C]

Example 36 cis-7-(2-Chloro-6-fluorophenyl)-5-(3,4-dimethylphenyl)-4,5,6,7-tetrahydro-[1,2,4]triazolo[1,5-a]pyrimidine. Yield: 88%. m.p. 223° C. Rf=0.25 (EtOAc/Hexanes 75:25). MS: MH+=357. $^1$H NMR (500 MHz, DMSO-d$_6$): δ 7.41-7.12 (m, 7H, CHar), 5.97-5.92 (m, 1H, CH), 4.69 (d, J=10.5 Hz, 1H, CH), 2.46-2.14 (m, 2H, CH2, overlapped with the peaks of two CH3), 2.23 (s, 3H, CH$_3$, overlapped with the peaks of CH2), 2.20 (s, 3H, CH$_3$, overlapped with the peaks of CH$_2$). HPLC: 99.7% (Method A, tR=3.95 min).

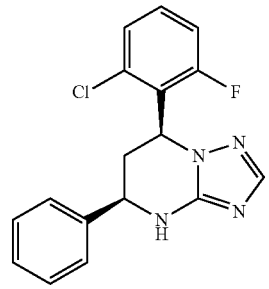 [SMILES: Fc1cccc(Cl)c1[C@@H]1C[C@H](c2ccccc2)Nc2ncnn21]

Example 37 cis-7-(2-Chloro-6-fluorophenyl)-5-phenyl-4,5,6,7-tetrahydro-[1,2,4]triazolo[1,5-a]pyrimidine. Yield: 82%. m.p. 270-271° C. Rf=0.26 (EtOAc/Hexanes 75:25). MS: MH+=329. $^1$H NMR (500 MHz, DMSO-d$_6$): δ 7.50-7.15 (m, 9H, CHar), 5.99-5.94 (m, 1H, CH), 4.80-4.76 (m, 1H, CH), 2.48-2.16 (m, 2H, CH2). HPLC: 99.5% (Method A, tR=3.05 min).

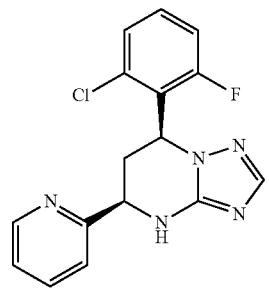 [SMILES: Fc1cccc(Cl)c1[C@@H]1C[C@H](c2ccccn2)Nc2ncnn21]

Example 38 cis-7-(2-Chloro-6-fluorophenyl)-5-(pyridin-2-yl)-4,5,6,7-tetrahydro-[1,2,4]triazolo[1,5-a]pyrimidine. Yield: 65%. m.p. 232° C. Rf=0.08 (EtOAc/Hexanes 90:10). MS: MH+=330. ¹H NMR (500 MHz, DMSO-d₆): δ 8.56-8.54 (m, 1H, CHar), 7.87-7.83 (m, 1H, CHar), 7.60-7.13 (m, 6H, CHar), 6.05-5.99 (m, 1H, CH), 4.88-4.85 (m, 1H, CH), 2.60-2.23 (m, 2H, CH₂, overlapped with the peaks of DMSO). HPLC: 99.7% (Method A, tR=2.24 min).

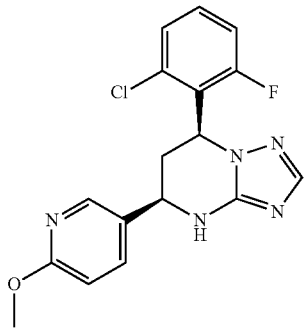 [SMILES: COc1ccc([C@H]2C[C@@H](c3c(F)cccc3Cl)n3ncnc3N2)cn1]

Example 39 cis-7-(2-Chloro-6-fluorophenyl)-5-(6-methoxypyridin-3-yl)-4,5,6,7-tetrahydro-[1,2,4]triazolo[1,5-a]pyrimidine. Yield: 64%. m.p. 230-221° C. Rf=0.14 (EtOAc/Hexanes 90:10). MS: MH+=360. ¹H NMR (500 MHz, DMSO-d₆): δ 8.22 (d, J=2.0 Hz, 1H, CHar), 7.79-7.77 (m, 1H, CHar), 7.48-7.16 (m, 4H, CHar), 6.86-6.82 (m, 1H, CHar), 5.98-5.93 (m, 1H, CH), 4.79-4.75 (m, 1H, CH), 3.85 (s, 3H, OCH₃), 2.47-2.20 (m, 2H, CH₉). HPLC: 95.0% (Method A, tR=2.61 min).

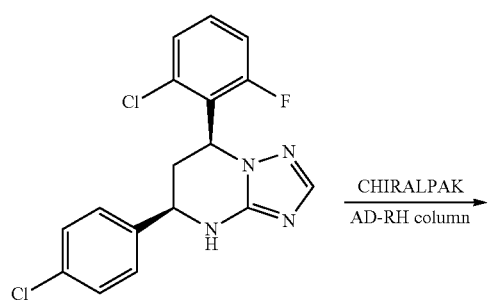

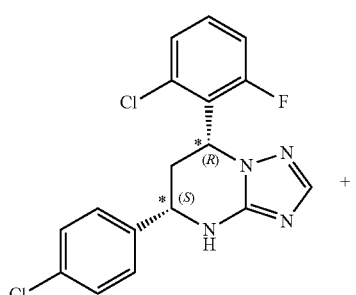

Example 40a

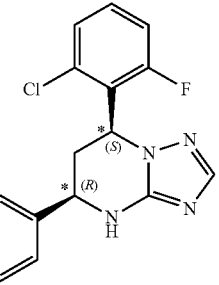

Example 40b

Example 40

Chiral resolution of cis-7-(2-Chloro-6-fluorophenyl)-5-(4-chlorophenyl)-4,5,6,7-tetrahydro-[1,2,4]triazolo[1,5-a]pyrimidine: Chiral resolution of 7-(2-Chloro-6-fluorophenyl)-5-(4-chlorophenyl)-4,5,6,7-tetrahydro[1,2,4]triazolo[1,5a]pyrimidine was carried out on the Waters 2695 HPLC instrument, equipped with CHIRALPAK® AD-RH column. Eluent system was: 30% A (H₂O), 70% B (EtOH); flow rate=0.5 mL/min; A=219 nm. The two enantiomers, 40a, (R,S)-7-(2-Chloro-6-fluoro-phenyl)-5-(4-chloro-phenyl)-4,5,6,7-tetrahydro-[1,2,4]triazolo[1,5-a]pyrimidine, and 40b, (S,R)-7-Chloro-6-fluoro-phenyl)-5-(4-chloro-phenyl)-4,5,6,7-tetrahydro-[1,2,4]triazolo[1,5-a]pyrimidine were isolated by removal of the solvents from peaks eluted at 43.5 minutes and 57.8 minutes respectively. 40a, (R,S)-7-(2-Chloro-6-fluoro-phenyl)-5-(4-chloro-phenyl)-4,5,6,7-tetrahydro-[1,2,4]triazolo[1,5-a]pyrimidine: Rf=0.16 (EtOAc/Hexanes 33.3:66.7). MS: MH+=363. 1H NMR (500 MHz, DMSO-d6): δ 7.54-7.15 (m, 8H, CHar), 5.98-5.94 (m, 1H, CH), 4.82-4.78 (m, 1H, CH), 2.47-2.13 (m, 2H, CH₂). HPLC: 99.8% (Method A, tR=3.67 min), CHIRALPAK® AD-RH column Rf=43.5 minutes. 40b, (S,R)-7-(2-Chloro-6-fluoro-phenyl)-5-(4-chloro-phenyl)-4,5,6,7-tetrahydro-[1,2,4]triazolo[1,5-a]pyrimidine: Rf=0.16 (EtOAc/Hexanes 33.3:66.7). MS: MH+=363. ¹H NMR (500 MHz, DMSO-d₆): δ 7.54-7.15 (m, 8H, CHar), 5.98-5.94 (m, 1H, CH), 4.82-4.78 (m, 1H, CH), 2.47-2.13 (m, 2H, CH2). HPLC: 99.8% (Method A, tR=3.67 min), CHIRALPAK® AD-RH column Rf=57.8 minutes.

Procedures

The following procedures can be utilized in evaluating and selecting compounds that reduces the serum level of hepatitis B surface antigen (HBsAg).

Generation and Testing of Drug-resistant HBV Variants: The plasmid pTREHBV, encoding the HBV genome of ayw serotype (Guo, H.; Jiang, D.; Zhou, T.; Cuconati, A.; Block, T. M.; Guo, J. T., 2007) was used as the background wild type construct. Standard molecular biology procedures employing the GeneTailor site-directed mutagenesis system (Invitrogen, Carlsbad Calif.) were used to generate single or double point mutations that give rise to the following amino acid changes in the polymerase open reading frame: A529V, N584T, M5521, M552V, L528M/M552V, and L528M/

M552V/T532G/55501 (Seeger, C.; Mason, W. S., 2000; Yotsuyanagi, H.; Koike, K., 2007). To generate the double and quadruple mutants, nucleotide substitutions were introduced sequentially by generating single mutations, confirming the sequence, and introducing additional mutations into the intermediate construct. All constructs were confirmed by sequencing through Integrated DNA technologies (Coralville Iowa). Primer sequences SEQ ID NO 1 through SEQ ID NO 17 were used for mutagenesis.

Transient expression of HBsAg from the mutant and wildtype HBV constructs was accomplished through transient transfection of plasmids into HepG2 cells seeded on 75 cm$^2$ flasks, using Lipofectamine 2000 reagent (Invitrogen) according to directions. 24 hours following transfection, cells were harvested by trypsinization and reseeded into 96-well plates at a density of 5×10$^5$ cells/well. 24 hours later media in each well was replaced with media containing test compounds in concentrations ranging (in half-log steps) from 0.016 to 50.0×10$^{-6}$ M, in 0.5% DMSO. Control wells contained DMSO alone. Each compound concentration was tested in duplicate. HBsAg levels was determined by ELISA Assay (Dougherty, A. M.; Guo, H.; Westby, G.; Liu, Y.; Simsek, E.; Guo, J.; Mehta, A.; Norton, P. G., B.; Block, T.; Cuconati, A. 2007), and EC50 values were calculated. For each mutant HBV genome, compounds were tested at least 5 and up to 10 times, allowing calculation of standard deviation.

HBsAg ELISA capture wells were made by incubation of 25 μL of commercial monoclonal anti-HBsAg (clone M701077, Fitzgerald Industries, Concord Mass.) diluted in binding buffer (0.17% Na2CO3, 0.29% NaHCO$_3$, pH 9.6) to 0.9 mg/ml, in each well of polystyrene 96-well plates. Incubation was at 4° C. overnight, followed by washing twice with 150 μL/well of PBS/0.5% Tween 20 (PBST) with shaking Capture wells were blocked with 150 μL PBST/2.0% BSA at 37° C. for 1 hr, followed by washing twice as described above. Following the second wash, cell culture supernatants from cell plates containing compounds were transferred and processed as described below.

Following compound addition, cell plates were incubated at 37° C. in 5.0% CO$_2$ atmosphere for six days. Following incubation, 150 μL of media from each well was transferred to blocked ELISA capture plates prepared as detailed above, and incubated for 4 days at 4° C. Media was removed, plates were washed, and 25 μL/well of detection antibody (horseradish peroxidase-conjugated anti-surface antigen mouse monoclonal antibody from Auzyme ELISA kit, Abbott Diagnostics, Abbott Park, Ill.), diluted to 0.625 ng/ml in PBST/2.0% BSA, was added. Plates were incubated at 37° C. for 1 hr., washed twice with 150 μL/well of PBST, with shaking, and 50 μL/well of BM Blue POD substrate (POD, Roche, Indianapolis, Ind.) was added. Plates were allowed to develop at room temperature a minimum of 20 minutes, and color change was determined by absorbance colorimetry in a SLT Rainbow spectrophotometer (Tecan US, Research Triangle Park, N.C.) at 650 nm with a reference wavelength of 490 nm, and best fit curve analysis of results with XLfit 4.0 (IDBS; Bridgewater, N.J.). Degree of inhibition was calculated against multiple negative control samples where only DMSO was incubated with cells. In addition each plate had multiple wells containing 1.0 mM DTT as a reference inhibitor. Only curves with $R^2$ values of above 0.5 were considered to produce valid $EC_{50}$ values.

Results for representative compounds according to the present invention are listed in Table 2 and Table 3 below.

TABLE 2

Examples of Selected Compounds from Formulas I, II, III, IV, V and VI and their Potencies for Biological Activity in Wild Type HBV

| Example number | ELISA, $EC_{50}$ (uM)* |
|---|---|
| 1 | 2.3 ± 2.1 |
| 2 | 1.8 ± 1.2 |
| 3 | 1.4 ± 0.4 |
| 4 | 3.6 ± 2.0 |
| 5 | 7.8 ± 3.2 |
| 6 | 2.2 ± 0.9 |
| 7 | 2.5 ± 1.2 |
| 8 | 3.0 ± 1.6 |
| 9 | 3.2 ± 1.2 |
| 10 | 8.9 ± 3.6 |
| 11 | 2.8 ± 2.1 |
| 12 | 3.1 ± 1.4 |
| 13 | 2.3 ± 1.3 |
| 14 | 2.6 ± 0.9 |
| 15 | 2.8 ± 2.0 |
| 16 | 1.7 ± 1.1 |
| 17 | >50 |
| 18 | 4.1 ± 2.1 |
| 19 | 4.7 ± 1.9 |
| 20 | 2.7 ± 1.0 |
| 21 | 2.7 ± 0.7 |
| 22 | 3.0 ± 0.7 |
| 23 | 8.8 ± 3.2 |
| 24 | 34.2 ± 13.6 |
| 25 | 3.2 ± 1.8 |
| 26 | 12.1 ± 3.6 |
| 27 | 5.9 ± 3.3 |
| 28 | 2.1 ± 1.0 |
| 29 | 7.4 ± 1.7 |
| 30 | 46.6 ± 3.2 |
| 31 | 3.0 ± 1.3 |
| 32 | 2.9 ± 0.7 |
| 33 | 5.2 ± 1.9 |
| 34 | 5.7 ± 1.9 |
| 35 | 11.2 ± 2.2 |
| 36 | 2.2 ± 0.5 |
| 37 | 40.8 ± 15.9 |
| 38 | >50 |
| 39 | >50 |
| 40a | 4.2 ± 1.6 |
| 40b | 35.6 ± 15.3 |

*EC50: 50% effective concentration, measured by the HBsAg ELISA assay in HepG2 stably transfected with wildtype HBV construct (HepG2.2.15).

TABLE 3

Examples of Selected Compounds from Formulas I, II, III, IV, V and VI and their Potencies for Biological Activity in Resistant HBV

| | Resistance Phenotype | | | |
|---|---|---|---|---|
| | None | Adefovir | Lamivudine/Telbivudine Genotype | Entecavir |
| Example Number | Wild Type | A529V | N584T | M552I | L528M/M552V | L528M/M552V/T532G/ EC$_{50}$ (μM)** |
| 1 | 8.4 ± 2.3 | 5.8 ± 1.7 | 5.6 ± 1.8 | 9.1 ± 1.8 | 10.3 ± 8.2 | 8.3 ± 1.3 |
| 25 | 6.9 ± 0.6 | 1.8 ± 0.5 | 6.4 ± 0.4 | 4.0 ± 0.5 | 8.5 ± 1.2 | 8.4 ± 3.7 |

*EC$_{50}$: 50% effective concentration, measured by the HBsAg ELISA assay in HepG2 transiently transfected with resistant HBV constructs.

SEQUENCE LISTING

| Sequence I.D. Number | Nucleotide Sequence |
|---|---|
| SEQ ID NO 1 | GCCTCAGCCC GTTTCTCCTG GTTCAGTTTA CTAG |
| SEQ ID NO 2 | CAGGAGAAAC GGGCTGAGGC CCACTCCCAT |
| SEQ ID NO 3 | CCAATTTTCT TTTGTCTTTG GGTGTACATT TAACCCCTAA CAAAAC |
| SEQ ID NO 4 | ACCCAAAGACAAAAGAAAATTGGTAACAGCGGT |
| SEQ ID NO 5 | GTTGCTGTAC CAAACCTTCG G |
| SEQ ID NO 6 | GTTCTTGTGG CAATGACCC |
| SEQ ID NO 7 | GTCTTTGGGT ATACATTTAA CCCCTAACAA AAC |
| SEQ ID NO 8 | TAAATGTATA CCCAAAGACA AAAGAAAATT G |
| SEQ ID NO 9 | GGGCCTCAGC CCGTTTCTCA TGGCTCAGTT TAC |
| SEQ ID NO 10 | GAGAAACGGG CTGAGGCCCA CTCCCATAGG |
| SEQ ID NO 11 | CACTGTTTGG CTTTCAGTTA TGTGGATGAT GTGGT |
| SEQ ID NO 12 | ATAACTGAAA GCCAAACAGT GGGGGAAAGC C |
| SEQ ID NO 13 | CACTGTTTGG CTTTCAGTTA TATCGATGAT GTGGT |
| SEQ ID NO 14 | CGTTTCTCAT GGCTCAGTTT GGTAGTGCCA TTTC |
| SEQ ID NO 15 | AAACTGAGCC ATGAGAAACG GGCTGAGGCC |
| SEQ ID NO 16 | CCCCCACTGT TTGGCTTTCA TTTATGTGGA TG |
| SEQ ID NO 17 | GAAAGCCAAA CAGTGGGGGA AGCCCTACG |

What is claimed:

1. A pharmaceutical composition comprising a pharmaceutically acceptable carrier and the R-enantiomer of at least one selected from the group consisting of:
   7-(2-Chloro-6-fluorophenyl)-5-(4-chlorophenyl)-4,7-dihydro-[1,2,4]triazolo[1,5-a]-pyrimidine;
   5-(4-Chlorophenyl)-7-(2,6-dichlorophenyl)-4,7-dihydro-[1,2,4]triazolo[1,5-a]pyrimidine;
   5-(4-Chlorophenyl)-7-(2,6-difluorophenyl)-4,7-dihydro-[1,2,4]triazolo[1,5-a]pyrimidine;
   7-(2-Chloro-4-fluorophenyl)-5-(4-chlorophenyl)-4,7-dihydro-[1,2,4]triazolo[1,5-a]-pyrimidine;
   7-(2-Chloro-6-fluorophenyl)-5-(2-chlorophenyl)-4,7-dihydro-[1,2,4]triazolo[1,5-a]-pyrimidine;
   7-(2-Chloro-6-fluorophenyl)-5-(3-chlorophenyl)-4,7-dihydro-[1,2,4]triazolo[1,5-a]-pyrimidine;
   7-(2-Chloro-6-fluorophenyl)-5-(4-fluorophenyl)-4,7-dihydro-[1,2,4]triazolo[1,5-a]-pyrimidine;
   5-(4-Bromophenyl)-7-(2-chloro-6-fluorophenyl)-4,7-dihydro[1,2,4]triazolo[1,5-a]-pyrimidine;
   7-(2-Chloro-6-fluorophenyl)-5-(4-ethylphenyl)-4,7-dihydro-[1,2,4]triazolo[1,5-a]-pyrimidine;
   7-(2-Chloro-6-fluorophenyl)-5-(4-methoxyphenyl)-4,7-dihydro-[1,2,4]triazolo[1,5-a]-pyrimidine;
   5-([1,1'-Biphenyl]-4-yl)-7-(2-chloro-6-fluorophenyl)-4,7-dihydro-[1,2,4]triazolo[1,5-a]-pyrimidine;
   7-(2-Chloro-6-fluorophenyl)-5-(naphthalen-2-yl)-4,7-dihydro-[1,2,4]triazolo[1,5-a]-pyrimidine;
   7-(2-Chloro-6-fluorophenyl)-5-(3,4-dichlorophenyl)-4,7-dihydro-[1,2,4]triazolo[1,5-a]-pyrimidine;
   7-(2-Chloro-6-fluorophenyl)-5-(2,4-dichlorophenyl)-4,7-dihydro-[1,2,4]triazolo[1,5-a]-pyrimidine;
   7-(2-Chloro-6-fluorophenyl)-5-(2,4-difluorophenyl)-4,7-dihydro-[1,2,4]triazolo[1,5-a]-pyrimidine;
   7-(2-Chloro-6-fluorophenyl)-5-(3,4-dimethylphenyl)-4,7-dihydro-[1,2,4]triazolo[1,5-a]-pyrimidine; and
   7-(2-Chloro-6-fluorophenyl)-5-(4-chlorophenyl)[1,2,4]triazolo[1,5-a]pyrimidine.

2. The pharmaceutical composition of claim 1, comprising the R-enantiomer of at least one selected from the group consisting of:
   7-(2-Chloro-6-fluorophenyl)-5-(4-chlorophenyl)-4,7-dihydro-[1,2,4]triazolo[1,5-a]-pyrimidine; and
   5-(4-Chlorophenyl)-7-(2,6-difluorophenyl)-4,7-dihydro-[1,2,4]triazolo[1,5-a]pyrimidine.

3. A pharmaceutical composition comprising a pharmaceutically acceptable carrier and the S-enantiomer of at least one selected from the group consisting of:
   7-(2-Chloro-6-fluorophenyl)-5-(4-chlorophenyl)-4,7-dihydro-[1,2,4]triazolo[1,5-a]-pyrimidine;
   5-(4-Chlorophenyl)-7-(2,6-dichlorophenyl)-4,7-dihydro-[1,2,4]triazolo[1,5-a]pyrimidine;
   5-(4-Chlorophenyl)-7-(2,6-difluorophenyl)-4,7-dihydro-[1,2,4]triazolo[1,5-a]pyrimidine;
   7-(2-Chloro-4-fluorophenyl)-5-(4-chlorophenyl)-4,7-dihydro-[1,2,4]triazolo[1,5-a]-pyrimidine;
   7-(2-Chloro-6-fluorophenyl)-5-(2-chlorophenyl)-4,7-dihydro-[1,2,4]triazolo[1,5-a]-pyrimidine;
   7-(2-Chloro-6-fluorophenyl)-5-(3-chlorophenyl)-4,7-dihydro-[1,2,4]triazolo[1,5-a]-pyrimidine;
   7-(2-Chloro-6-fluorophenyl)-5-(4-fluorophenyl)-4,7-dihydro-[1,2,4]triazolo[1,5-a]-pyrimidine;
   5-(4-Bromophenyl)-7-(2-chloro-6-fluorophenyl)-4,7-dihydro[1,2,4]triazolo[1,5-a]-pyrimidine;
   7-(2-Chloro-6-fluorophenyl)-5-(4-ethylphenyl)-4,7-dihydro-[1,2,4]triazolo[1,5-a]-pyrimidine;
   7-(2-Chloro-6-fluorophenyl)-5-(4-methoxyphenyl)-4,7-dihydro-[1,2,4]triazolo[1,5-a]-pyrimidine;
   5-([1,1'-Biphenyl]-4-yl)-7-(2-chloro-6-fluorophenyl)-4,7-dihydro-[1,2,4]triazolo[1,5-a]-pyrimidine;
   7-(2-Chloro-6-fluorophenyl)-5-(naphthalen-2-yl)-4,7-dihydro-[1,2,4]triazolo[1,5-a]-pyrimidine;

7-(2-Chloro-6-fluorophenyl)-5-(3,4-dichlorophenyl)-4,7-dihydro-[1,2,4]triazolo[1,5-a]-pyrimidine;

7-(2-Chloro-6-fluorophenyl)-5-(2,4-dichlorophenyl)-4,7-dihydro-[1,2,4]triazolo[1,5-a]-pyrimidine;

7-(2-Chloro-6-fluorophenyl)-5-(2,4-difluorophenyl)-4,7-dihydro-[1,2,4]triazolo[1,5-a]-pyrimidine;

7-(2-Chloro-6-fluorophenyl)-5-(3,4-dimethylphenyl)-4,7-dihydro-[1,2,4]triazolo[1,5-a]-pyrimidine; and 7-(2-Chloro-6-fluorophenyl)-5-(4-chlorophenyl)[1,2,4]triazolo[1,5-a]pyrimidine.

4. The pharmaceutical composition of claim 3, comprising the S-enantiomer of at least one selected from the group consisting of:

7-(2-Chloro-6-fluorophenyl)-5-(4-chlorophenyl)-4,7-dihydro-[1,2,4]triazolo[1,5-a]-pyrimidine; and 5-(4-Chlorophenyl)-7-(2,6-difluorophenyl)-4,7-dihydro-[1,2,4]triazolo[1,5-a]pyrimidine.

5. A pharmaceutical composition comprising a pharmaceutically acceptable carrier and the R,S-isomer of at least one selected from the group consisting of:

cis-7-(2-Chloro-6-fluorophenyl)-5-(4-chlorophenyl)-4,5,6,7-tetrahydro-[1,2,4]triazolo[1,5-a]-pyrimidine;

cis-5-(4-Chlorophenyl)-7-(2,6-dichlorophenyl)-4,5,6,7-tetrahydro-[1,2,4]triazolo[1,5-a]-pyrimidine;

cis-5-(4-Chlorophenyl)-7-(2,6-difluorophenyl)-4,5,6,7-tetrahydro-[1,2,4]triazolo[1,5-a]-pyrimidine;

cis-7-(2-Chloro-4-fluorophenyl)-5-(4-chlorophenyl)-4,5,6,7-tetrahydro-[1,2,4]triazolo[1,5-a]-pyrimidine;

cis-7-(2-Chlorophenyl)-5-(4-chlorophenyl)-4,5,6,7-tetrahydro-[1,2,4]triazolo[1,5-a]-pyrimidine;

cis-5-(4-Chlorophenyl)-7-(4-isopropylphenyl)-4,5,6,7-tetrahydro-[1,2,4]triazolo[1,5-a]-pyrimidine;

cis-5-(4-Chlorophenyl)-7-phenyl-4,5,6,7-tetrahydro-[1,2,4]triazolo[1,5-a]pyrimidine;

cis-7-(2-Chloro-6-fluorophenyl)-5-(2-chlorophenyl)-4,5,6,7-tetrahydro-[1,2,4]triazolo[1,5-a]-pyrimidine;

cis-7-(2-Chloro-6-fluorophenyl)-5-(3-chlorophenyl)-4,5,6,7-tetrahydro-[1,2,4]triazolo[1,5-a]-pyrimidine;

cis-7-(2-Chloro-6-fluorophenyl)-5-(4-fluorophenyl)-4,5,6,7-tetrahydro-[1,2,4]triazolo[1,5-a]-pyrimidine;

cis-5-(4-Bromophenyl)-7-(2-chloro-6-fluorophenyl)-4,5,6,7-tetrahydro-[1,2,4]triazolo[1,5-a]-pyrimidine;

cis-7-(2-Chloro-6-fluorophenyl)-5-(4-ethylphenyl)-4,5,6,7-tetrahydro-[1,2,4]triazolo[1,5-a]-pyrimidine;

cis-7-(2-Chloro-6-fluorophenyl)-5-(4-methoxyphenyl)-4,5,6,7-tetrahydro-[1,2,4]triazolo[1,5-a]pyrimidine;

cis-5-([1,1'-Biphenyl]-4-yl)-7-(2-chloro-6-fluorophenyl)-4,5,6,7-tetrahydro-[1,2,4]-triazolo[1,5-a]pyrimidine;

cis-7-(2-Chloro-6-fluorophenyl)-5-(naphthalen-2-yl)-4,5,6,7-tetrahydro-[1,2,4]triazolo[1,5-a]-pyrimidine;

cis-7-(2-Chloro-6-fluorophenyl)-5-(3,4-dichlorophenyl)-4,5,6,7-tetrahydro-[1,2,4]-triazolo[1,5-a]pyrimidine;

cis-7-(2-Chloro-6-fluorophenyl)-5-(2,4-dichlorophenyl)-4,5,6,7-tetrahydro-[1,2,4]triazolo-[1,5-a]pyrimidine;

cis-7-(2-Chloro-6-fluorophenyl)-5-(2,4-difluorophenyl)-4,5,6,7-tetrahydro-[1,2,4]triazolo[1,5-a]pyrimidine;

cis-7-(2-Chloro-6-fluorophenyl)-5-(3,4-dimethylphenyl)-4,5,6,7-tetrahydro-[1,2,4]triazolo-[1,5-a]pyrimidine;

cis-7-(2-Chloro-6-fluorophenyl)-5-phenyl-4,5,6,7-tetrahydro-[1,2,4]triazolo[1,5-a]-pyrimidine;

cis-7-(2-Chloro-6-fluorophenyl)-5-(pyridin-2-yl)-4,5,6,7-tetrahydro-[1,2,4]triazolo[1,5-*a*]-pyrimidine; and cis-7-(2-Chloro-6-fluorophenyl)-5-(6-methoxypyridin-3-yl)-4,5,6,7-tetrahydro-[1,2,4]-triazolo[1,5-a]pyrimidine.

6. The pharmaceutical composition of claim 5, comprising the R,S-enantiomer of at least one selected from the group consisting of:

cis-7-(2-Chloro-6-fluorophenyl)-5-(4-chlorophenyl)-4,5,6,7-tetrahydro-[1,2,4]triazolo[1,5-a]-pyrimidine; and cis-5-(4-Chlorophenyl)-7-(2,6-difluorophenyl)-4,5,6,7-tetrahydro-[1,2,4]triazolo[1,5-a]-pyrimidine.

7. A pharmaceutical composition comprising a pharmaceutically acceptable carrier and the S,R-isomer of at least one selected from the group consisting of:

cis-7-(2-Chloro-6-fluorophenyl)-5-(4-chlorophenyl)-4,5,6,7-tetrahydro-[1,2,4]triazolo[1,5-a]-pyrimidine;

cis-5-(4-Chlorophenyl)-7-(2,6-dichlorophenyl)-4,5,6,7-tetrahydro-[1,2,4]triazolo[1,5-a]-pyrimidine;

cis-5-(4-Chlorophenyl)-7-(2,6-difluorophenyl)-4,5,6,7-tetrahydro-[1,2,4]triazolo[1,5-a]-pyrimidine;

cis-7-(2-Chloro-4-fluorophenyl)-5-(4-chlorophenyl)-4,5,6,7-tetrahydro-[1,2,4]triazolo[1,5-a]-pyrimidine;

cis-7-(2-Chlorophenyl)-5-(4-chlorophenyl)-4,5,6,7-tetrahydro-[1,2,4]triazolo[1,5-a]-pyrimidine;

cis-5-(4-Chlorophenyl)-7-(4-isopropylphenyl)-4,5,6,7-tetrahydro-[1,2,4]triazolo[1,5-a]-pyrimidine;

cis-5-(4-Chlorophenyl)-7-phenyl-4,5,6,7-tetrahydro-[1,2,4]triazolo[1,5-a]pyrimidine;

cis-7-(2-Chloro-6-fluorophenyl)-5-(2-chlorophenyl)-4,5,6,7-tetrahydro-[1,2,4]triazolo[1,5-a]-pyrimidine;

cis-7-(2-Chloro-6-fluorophenyl)-5-(3-chlorophenyl)-4,5,6,7-tetrahydro-[1,2,4]triazolo[1,5-a]-pyrimidine;

cis-7-(2-Chloro-6-fluorophenyl)-5-(4-fluorophenyl)-4,5,6,7-tetrahydro-[1,2,4]triazolo[1,5-a]-pyrimidine;

cis-5-(4-Bromophenyl)-7-(2-chloro-6-fluorophenyl)-4,5,6,7-tetrahydro-[1,2,4]triazolo[1,5-a]-pyrimidine;

cis-7-(2-Chloro-6-fluorophenyl)-5-(4-ethylphenyl)-4,5,6,7-tetrahydro-[1,2,4]triazolo[1,5-a]-pyrimidine;

cis-7-(2-Chloro-6-fluorophenyl)-5-(4-methoxyphenyl)-4,5,6,7-tetrahydro-[1,2,4]triazolo[1,5-a]pyrimidine;

cis-5-([1,1'-Biphenyl]-4-yl)-7-(2-chloro-6-fluorophenyl)-4,5,6,7-tetrahydro-[1,2,4]-triazolo[1,5-a]pyrimidine;

cis-7-(2-Chloro-6-fluorophenyl)-5-(naphthalen-2-yl)-4,5,6,7-tetrahydro-[1,2,4]triazolo[1,5-a]-pyrimidine;

cis-7-(2-Chloro-6-fluorophenyl)-5-(3,4-dichlorophenyl)-4,5,6,7-tetrahydro-[1,2,4]-triazolo[1,5-a]pyrimidine;

cis-7-(2-Chloro-6-fluorophenyl)-5-(2,4-dichlorophenyl)-4,5,6,7-tetrahydro-[1,2,4]triazolo-[1,5-a]pyrimidine;

cis-7-(2-Chloro-6-fluorophenyl)-5-(2,4-difluorophenyl)-4,5,6,7-tetrahydro-[1,2,4]triazolo[1,5-a]pyrimidine;

cis-7-(2-Chloro-6-fluorophenyl)-5-(3,4-dimethylphenyl)-4,5,6,7-tetrahydro-[1,2,4]triazolo-[1,5-a]pyrimidine;

cis-7-(2-Chloro-6-fluorophenyl)-5-phenyl-4,5,6,7-tetrahydro-[1,2,4]triazolo[1,5-a]-pyrimidine;

cis-7-(2-Chloro-6-fluorophenyl)-5-(pyridin-2-yl)-4,5,6,7-tetrahydro-[1,2,4]triazolo[1,5-*a*]-pyrimidine; and cis-7-(2-Chloro-6-fluorophenyl)-5-(6-methoxypyridin-3-yl)-4,5,6,7-tetrahydro-[1,2,4]-triazolo[1,5-a]pyrimidine.

8. The pharmaceutical composition of claim 7, comprising the S,R-enantiomer of at least one selected from the group consisting of:

cis-7-(2-Chloro-6-fluorophenyl)-5-(4-chlorophenyl)-4,5,6,7-tetrahydro-[1,2,4]triazolo[1,5-a]-pyrimidine; and cis-5-(4-Chlorophenyl)-7-(2,6-difluorophenyl)-4,5,6,7-tetrahydro-[1,2,4]triazolo[1,5-a]-pyrimidine.

9. The composition of claims 1, further comprising an antiviral compound.

10. The composition of claim 9, wherein the antiviral compound is a nucleoside antiviral compound, a nucleotide antiviral compound, or any mixtures thereof.

11. A method for treating a hepatitis virus infection in a patient, the method comprising administering an effective amount of the composition of claim 1 to a patient in need thereof.

12. The method of claim 11, wherein the hepatitis virus is a hepadnaviridae family virus or hepatitis delta virus.

13. The method of claim 11, wherein the hepatitis virus is hepatitis B virus.

* * * * *